United States Patent
Winnik et al.

(10) Patent No.: US 10,752,707 B2
(45) Date of Patent: *Aug. 25, 2020

(54) POLYMER BACKBONE ELEMENT TAGS

(71) Applicant: Fluidigm Canada Inc., Markham (CA)

(72) Inventors: Mitchell A. Winnik, Toronto (CA); Mark Nitz, Toronto (CA); Vladimir Baranov, Richmond Hill (CA); Xudong Lou, Richmond Hill (CA)

(73) Assignee: FLUIDIGM CANADA INC., Markham (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/506,243

(22) Filed: Jul. 9, 2019

(65) Prior Publication Data
US 2019/0345272 A1    Nov. 14, 2019

Related U.S. Application Data

(60) Continuation of application No. 16/047,927, filed on Jul. 27, 2018, which is a continuation of application
(Continued)

(51) Int. Cl.
*G01N 33/532* (2006.01)
*C08F 8/42* (2006.01)
(Continued)

(52) U.S. Cl.
CPC ............ *C08F 8/32* (2013.01); *C08F 8/14* (2013.01); *C08F 8/42* (2013.01); *C08F 220/36* (2013.01);
(Continued)

(58) Field of Classification Search
CPC .. C08F 8/42; C08F 220/36; C08F 8/32; C08F 220/56; C08F 8/14; G01N 33/532; G01N 33/58; G01N 33/57426; Y10T 436/24
See application file for complete search history.

(56) References Cited

U.S. PATENT DOCUMENTS 4,962,045 A * 10/1990 Picozza ............... C12Q 1/6816
                                                    436/501
5,256,535 A * 10/1993 Ylikoski .............. C12Q 1/6816
                                                    435/6.13
(Continued)

FOREIGN PATENT DOCUMENTS

WO    2002/054075 A1    7/2002
WO    2004/059291 A2    7/2004
(Continued)

OTHER PUBLICATIONS

Bunzli et al. Taking advantage of luminescent lanthanide ions. Chem. Soc. Rev., 2005, vol. 34, pp. 1048-1077. (Year: 2005).*
(Continued)

*Primary Examiner* — Shafiqul Haq
(74) *Attorney, Agent, or Firm* — Kilpatrick Townsend & Stockton LLP

(57) ABSTRACT

Element tags based on novel metal-polymer conjugates are provided for elemental analysis of analytes, including ICP-MS. A polymer backbone is functionalized to irreversibly bind metals that are selected prior to use by the user. The polymer is further functionalized to attach a linker which allows for attachment to antibodies or other affinity reagents. The polymer format allows attachment of many copies of a given isotope, which linearly improves sensitivity. The metal-polymer conjugate tags enable multiplexed assay in two formats: bulk assay, where the average biomarker distribution in the sample is diagnostic, and single cell format to distinguish a rare (for example a diseased) cell in a complex sample (for example, blood).

15 Claims, 16 Drawing Sheets

Related U.S. Application Data

No. 14/875,553, filed on Oct. 5, 2015, now Pat. No. 10,072,104, which is a division of application No. 14/659,224, filed on Mar. 16, 2015, now Pat. No. 9,296,838, which is a division of application No. 11/754,340, filed on May 28, 2007, now Pat. No. 9,012,239.

(60) Provisional application No. 60/803,356, filed on May 27, 2006.

(51) Int. Cl.

| | | |
|---|---|---|
| C08F 8/32 | (2006.01) | |
| C08F 220/36 | (2006.01) | |
| G01N 33/58 | (2006.01) | |
| C08F 8/14 | (2006.01) | |
| C08F 220/56 | (2006.01) | |
| G01N 33/574 | (2006.01) | |

(52) U.S. Cl.
CPC ......... *C08F 220/56* (2013.01); *G01N 33/532* (2013.01); *G01N 33/57426* (2013.01); *G01N 33/58* (2013.01); *Y10T 436/24* (2015.01)

(56) References Cited

U.S. PATENT DOCUMENTS

| | | | |
|---|---|---|---|
| 5,554,748 A | 9/1996 | Sieving et al. | |
| 5,914,095 A | 6/1999 | Watson | |
| 6,031,074 A | 2/2000 | Saxinger | |
| 6,203,775 B1* | 3/2001 | Torchilin | C07K 1/13 424/1.11 |
| 6,241,968 B1 | 6/2001 | Tournier et al. | |
| 6,599,711 B2 | 7/2003 | Crouch et al. | |
| 6,846,645 B2 | 1/2005 | Xue et al. | |
| 7,094,860 B2 | 8/2006 | Inaba et al. | |
| 9,012,239 B2* | 4/2015 | Winnik | C08F 8/42 436/528 |
| 9,296,838 B2* | 3/2016 | Winnik | C08F 8/42 |
| 10,072,104 B2* | 9/2018 | Winnik | C08F 8/42 |
| 2004/0043030 A1 | 3/2004 | Griffiths et al. | |
| 2004/0072250 A1* | 4/2004 | Baranov | G01N 33/532 435/7.1 |
| 2004/0248801 A1 | 12/2004 | Kiessling et al. | |
| 2004/0258614 A1 | 12/2004 | Line et al. | |
| 2005/0118105 A1 | 6/2005 | Platzek et al. | |
| 2005/0218139 A1 | 10/2005 | Bandura et al. | |
| 2005/0227290 A1 | 10/2005 | Lippard et al. | |
| 2007/0054304 A1 | 3/2007 | Agnew et al. | |
| 2007/0238143 A1 | 10/2007 | Xia et al. | |
| 2008/0193377 A1 | 8/2008 | Line et al. | |
| 2015/0183895 A1 | 7/2015 | Winnik et al. | |
| 2019/0077890 A1* | 3/2019 | Winnik | C08F 8/42 |

FOREIGN PATENT DOCUMENTS

| | | |
|---|---|---|
| WO | 2005/003767 A2 | 1/2005 |
| WO | 2005/047901 A2 | 5/2005 |
| WO | 2005/093784 A1 | 10/2005 |
| WO | 2005/098415 A1 | 10/2005 |
| WO | 2005/123959 A2 | 12/2005 |
| WO | 2007/093049 A2 | 8/2007 |

OTHER PUBLICATIONS

Liu et al. Bifunctional chelators for therapeutic lanthanide radiopharmaceuticals. Bioconjugate Chem., 2001, vol. 12, No. 1, pp. 7-34. (Year: 2001).*

Ban Dura, D.R., et al., "Characterization of Phosphorus Content of Biological Samples by ICP-DRC-MS: Potential Tool for Cancer Research," 2004, J Anal At Spectrom, 19:96-100.

Baranov, V.I., et al., "A Sensitive and Quantitative Element-Tagged Immunoassay with ICPMS Detection," 2002, Analyt Chem, 74/7:1629-1636.

Chen, C., et al., "Biosensors of Protein Kinase Action: From in vitro Assays to Living Cells," 2004, Biochimica et Biophysica Acta, 1697/1-2:39-51.

Chiefari et al. "Living free-radical polymerization by reversible addition-fragmentation chain transfer: the RAFT process," Macromolecules, 1998, 31:5559-5562.

Cooper, J.A., et al., "The When and How of Src Regulation," 1993, Cell, 73:1051-1054.

Davtyan et al. Effect fo adriamycin and its complexes with transition metals on induction of immune response of human lymphocytes in culture. Bulletin of Experimental Biology and Medicine 1999, vol. 128, No, 7, pp. 710-712.

Gao, YW, et al., "DNA-Modified Core-Shell Ag/Au Nanoparticles," 2001, JAm Chem Soc, 123/32:7961-7962.

Gaudet, E., et al., "A Homogeneous Fluorescence Polarization assay Adaptable for a Range of Protein Serine/Threonine and Tyrosine Kinases," 2003, J Biomel Screening, 8/2:164-175.

Hackel, P.O., et al., "Epidermal Growth Factor Receptors: Critical Mediators of Multiple Receptor Pathways," 1999, Current Opinion in Cell Biology, 11:184-189.

Huff et al. Imidazole- and alkylamine-ligated iron(II, III) chlorin complexes as meodel for histidine and lysine coordination to iron in dihydroporphyrin-containing proteins: characterization with magnetic circular dichroism spectroscopy. Inorg. Chem. 1993, vol. 32, pp. 1460-1466.

International Preliminary Report on Patentability issued in PCT/CA2007/000222, dated Aug. 19, 2008.

International Search Report issued in PCT/CA2007/000222, dated May 23, 2007.

Kellar et al. High relaxivity linear Gd(DTPA)-polymer conjugates: the role of hydrophobic interactions. Magn Reson Med 1997, vol. 38, No. 5, pp. 712-716.

Kopecek et al. HPMA copolymer-anticancer drug conjugates: design, activity, and mechanism of action. European Journal of Pharmaceutics and Biopharmaceutics, 2000, Vo.50, pp. 61-81.

Larsen, M.R., et al., "Highly Selective Enrichment of Phosphorylated Peptides from Peptide Mixtures Using TitaniumDioxide Microcolumns," 2005, Malec. and Cell Proteomics, 4:873-886.

Mandell, J. W., "Phosphorylation State-Specific Antibodies: Applications in Investigative and Diagnostic Pathology," 2003, Am. J. of Pathology, 163:1687-1698.

Merkoci, A., et al., "Toward an ICPMS-Linked DNA Assay Based on Gold Nanoparticles Immunoconnected Through Peptide Sequences," 2005, Anal Chem, 77:6500-6503.

Meyer, T.J., et al., "Molecular-Level Electron Transfer and Excited State Assemblies on Surfaces of Metal Oxides and Glass," 1994, Inorg Chem, 33:3952-3964.

Ornatsky, 0., et al., "Messenger RNA Detection in Leukemia Cell Lines by Novel Metal-Tagged in situ Hybridization Using Inductively Coupled Plasma Mass Spectrometry," 2006, Translational Oncogenomics, 1-9.

Ornatsky. 0. et al.. "Multiple Cellular Antigen Detection by ICP-MS", 2006, J. of Immun. Meth., 308:68-76.

Quinn, Z.A., et al., "Simultaneous Determination of Proteins Using an Element-Tagged Immunoassay Coupled with ICP-MS Detection," 2002, JAAS, 17:892-896.

Schlosser, A., et al., "Mapping of Phosphorylation sites by a Multi-Protease Approach with Specific Phosphopeptide Enrichment and NanoLC-MS/MS Analysis," 2005, Anal Chem, 77:5243-5250.

Shunmugam et al. Efficient route to well-characterized homo block, and statistical polymers containing terpyridine in the side chain. Journal of Polymer Science 2005, vol. 43, pp. 5831-5843.

Tew, G.N., et al., "Incorporation of Terpyridine into the Side Chain of Copolymers to Create Multi-Functional Materials," 2005, Polymer, 46:8440-8447.

Thomas, R.N., et al., "Nanosphere-Antibody Conjugates with Releasable Fluorescent Probes," 2001, Fresenius J Anal Chem, 369:477-482.

Torchilin, V. P., "Polymeric Contrast Agents for Medical Imaging", Curr Pharm Biotechnol (2000) 1:183-215.

(56) References Cited

OTHER PUBLICATIONS

Written Opinion issued in PCT/CA2007/000222, dated May 14, 2007.

Zhang et. al. Simultaneous determination of alpha-fetoprotein and free beta-human chronic gonadotropin by element-tagged immunoassay with detection by inductively coupled plasma mass spectrometry. Clinical Chemistry 2004, vol. 50, No. 7, pp. 1214-1221. (Year: 2004).

Zong et al. Effect of size and charge on pharmacokinetics and in vivo MRI contrast enhancement of biodegradable polydisulfide GD(III) complexes. Journal of Controlled Release 2006, vol. 112, pp. 350-356.

Weissleder, et al., Size Optimization of Synthetic Graft Copolymers for in Vivo Angiogenesis Imaging, Bioconjugate Chemistry, vol. 12, No. 2, pp. 213-219, Mar. 6, 2001.

\* cited by examiner

Scheme 9.
Structure of the monomers, *N-acryloxysuccinimide* (NAS), *N,N*-dimethylacrylamide (DMA) and of chain transfer agent, *tert*-butyl dithiobenzoat (*t*-BDB)

Figure 8

| Ratio of NAS/DMA Mol% Wt% | | $[M]_0$ /$[CTA]_0$ | $[CTA]_0$ /$[AMBN]_0$ | Reaction time (h) | Polymer yield | $M_{n,GPC}$ | $M_w/M_n$ |
|---|---|---|---|---|---|---|---|
| 13 | 20 | 70 | 1.4 | 18 | 75% | 6500 | 1.45 |
| 47 | 60 | 55 | 1.5 | 18 | 80% | 8298 | 1.50 |
| 60 | 72 | 70 | 3 | 18 | 80% | 8000 | 1.15 |

CTA: Chain transfer agent, $t$-BDB. $[M]_0$: Starting monomer concentration. $M_{n,GPC}$: using polystyrene standards.

Scheme 10.

Preparation of ligand-polymer conjugate

Scheme 11.

Reaction of ligand-polymer conjugate with 1,4Bis(maleimido)butane

Scheme 12.
Preparation of DOTA based ligand-polymer conjugate a) triethylamine, DMF, amine 10, 14 h; b) Trifluoroacetic acid, 14 h;
c) (i) dithiothreitol, phosphate buffer pH 8.5, 50 C, 1 h,
(ii) 2,2'-(ethylenedioxy)bis(ethylmaleimide), DMF/H₂O, 1 h, RT a) Triethylamine, DMF, amine 14; b) Trifluoroacetic acid; c) DTPA succinimidic ester, Solution A; d) (i) Tris(2-carboxyethyl)phosphine (TCEP), phosphate buffer solution (PBS, pH 7.2), (ii) 2,2'-(ethylenedioxy)-bis(ethylmaleimide), DMF/H2O, 22 C.

a b

Flow Chart I

RAFT Polymerization Procedure

Flow Chart II

Polymer-DTPA-Linker attachment procedure (corresponding to Figure 9)

POLYMER BACKBONE ELEMENT TAGS

CROSS-REFERENCE TO RELATED APPLICATIONS

This application is a continuation of U.S. patent application Ser. No. 16/047,927, filed Jul. 27, 2018, which is a continuation of U.S. patent application Ser. No. 14/875,553, filed Oct. 5, 2015, now U.S. Pat. No. 10,072,104, which is a divisional of U.S. application Ser. No. 14/659,224, filed on Mar. 16, 2015, now U.S. Pat. No. 9,296,838, which is a divisional application of U.S. application Ser. No. 11/754,340 filed on May 28, 2007, now U.S. Pat. No. 9,012,239, which claims the benefit of U.S. Provisional Patent Application Ser. No. 60/803,356, entitled "Polymer Backbone Elemental Tags," filed May 27, 2006, the entire contents of which are incorporated by this reference.

COPYRIGHT AND LEGAL NOTICES

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

FIELD

The invention relates to a new class of tagged biomolecules that have been specifically designed to operate in conjunction with elemental analysis detection, to provide high sensitivity multiplexed biomarker determinations.

INTRODUCTION

Technology that enables accurate protein quantitation is desired in the booming area of proteomics and drug discovery as well as in areas of clinical and diagnostic testing. It is also important in biological research aimed at analyzing protein synthesis, function and disease at the molecular level. Currently, there are several existing techniques that are widely used for estimating protein concentration including: Bradford and Lowry assays, UV spectroscopy, organic mass spectrometry, HPLC, flow cytometry, ligand binding assays, ELISA (Enzyme Linked Immunosorbent Assay), and RIA (RadioImmunoAssay). Nevertheless, this extensive assortment of well-established analytical tools and research techniques remains insufficient for today's challenges. The failures of these methods relate to limitations in sensitivity, selectivity, dynamic range, and the ability to determine the concentration of several proteins simultaneously in an accurate and absolute manner (multiplexing). The realization that elemental analysis offers significant advantages to the field of protein quantitation has directed the development of several new methods of protein quantitation via Inductively Coupled Plasma Mass Spectrometry (ICP-MS) linked immunoassays[1-4]. This new technique provides an innovative arena for ICP-MS in the analysis of biological samples[5,6]. The unique analytical properties of ICP-MS allow the selection of tags from the non-radioactive elements that do not naturally occur in biological samples.

Definitions

"Elemental analysis" is a process where a sample is analyzed for its elemental composition and/or isotopic composition. Elemental analysis can be accomplished by a number of methods, including, but not limited to:

(i) optical atomic spectroscopy, such as flame atomic absorption, graphite furnace atomic absorption, and inductively coupled plasma atomic emission, which probe the outer electronic structure of atoms;

(ii) mass spectrometric atomic spectroscopy, such as inductively coupled mass spectrometry, which probes the mass of atoms;

(iii) X-ray fluorescence, particle induced x-ray emission, x-ray photoelectron spectroscopy, and Auger electron spectroscopy which probes the inner electronic structure of atoms.

"Elemental analyzer" is an instrument for the quantitation of the atomic composition of a sample employing one of the methods of elemental analysis.

"Particle elemental analysis" is a process where a sample, composed of particles dispersed in a liquid (beads in buffer, or cells in growth media, or blood, for example), is interrogated in such manner that the atomic composition is recorded for individual particles (bead-by-bead, cell-by-cell, particle-by-particle, for example). An example of the analytical instrument is a mass spectrometer-based flow cytometer, ICP-TOF, or ICP-MS or any elemental analyzer configured to interrogate individual particles.

"Volume or bulk elemental analysis" is a process where an analyzed sample is interrogated in such manner that the atomic composition is averaged over the entire volume of the sample.

"An internal standard" is defined as a known amount of a compound, different from the analyte that is added to the unknown. Signal from analyte is compared with signal from the internal standard to find out how much analyte is present. An internal standard may be used when performing mass spectrometry quantitation. An internal standard can be also used by other means known to those skilled in the art.

"Biological sample" refers to any sample of a biological nature that requires analysis. For example, the sample may comprise or may be suspected of comprising biological molecules, tissue, fluid, and cells of an animal, plant, fungus, or bacteria. It also includes molecules of viral origin. Typical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Another typical source of biological samples are viruses and cell cultures of animal, plant, bacteria, fungi where gene expression states can be manipulated to explore the relationship among genes. Biological samples may also include solutions of biological molecules (either purified or not purified) such as proteins, peptides, antibodies, DNA, RNA, aptamers, polysaccharides, lipids, etc. Other examples are known to those skilled in the art.

"Antibodies" are immunoglobulin glycoprotein molecules found normally in serum of animals. Antibodies may be made in mammals such as rabbits, mice, rats, goats, etc., and chicken or may be made by recombinant methods as is known to those skilled in the art and described, for example, in U.S. Pat. No. 4,816,567. Procedures for immunization and elicitation of a high antibody production response in an animal are well known to those skilled in the art and can be found, for example, in Antibodies, A Laboratory Manual, Cold Spring Harbor Laboratory, 1988, pages 92-115. Antibodies may be used as whole molecules, fragments of molecules known as Fab' and Fab2' fragments, as monovalent antibodies (combining a light chain and a modified heavy chain), and other examples known in to those skilled in the art.

"Primary antibodies" are antibodies that bind specifically to an antigen injected into an animal. They can be extracted from the animal or can be made by recombinant means.

"Secondary antibodies" are those antibodies that bind specifically to primary antibodies. For example, primary antibodies can be used as the antigen injected into an animal of a different species, to generate secondary antibodies. For example, rabbit secondary anti-mouse antibodies can be made by immunizing a rabbit with mouse antibodies.

"Antigen" is a substance that stimulates an immune response in a host organism, especially the production of antibodies. Antigens are usually proteins or polysaccharides, but can be any type of molecule, including but not limited to, small molecules (haptens) coupled to a carrier-protein.

"Bio-markers" are molecules and constructs, which may for example be antigens, small molecules, nucleotides, oligonucleotides, DNA or RNA, that are present in the cell volume or on the cell surface of only one type of cell, or whose relative abundance is unique to that type of cell. Cell bio-markers can be used to distinguish that cell from other cells. For example, antigens present on the cell surface of only one type of cell are called cell surface bio-markers that distinguish that cell from other cells.

"Immunoassay" as used herein means an assay in which an analyte, such as cellular antigen or bio-marker, is detected by an affinity reagent such as a primary antibody. For example, an "immunoassay" can be an assay in which an analyte is detected by a tagged affinity reagent, such as a primary antibody conjugated to a metal tagged polymer.

"Biomolecule" as used herein means any biological molecule and includes small biomolecules, for example, but not limited to: Lipids, Phospholipids, Glycolipids, Sterols, Vitamins, Hormones, Neurotransmitters, Carbohydrates, Sugars, Disaccharides, Amino acids, Nucleotides, Phosphate, and Monosaccharides; and large biomolecules, for example but not limited to: Peptides, Oligopeptides, Polypeptides, Proteins, Nucleic acids, i.e. DNA, RNA, Oligosaccharides, Polysaccharides, and Prions. Other biomolecules are known to those skilled in the art and are encompassed in the applicant's teachings.

"Affinity reagent" is a biomolecule capable of tightly binding to a target molecule or analyte, for example an antigen or biomarker. For example, an antibody is an affinity reagent that recognizes and binds with high affinity to a specific antigen. Streptavidin is a protein molecule that specifically binds biotin and may be considered as another example of the affinity reagent. Other affinity reagents are known to those skilled in the art, and include, but are not limited to aptamers, oligonucleotides, protein molecules, lectins and polysaccharides.

"Tagged affinity reagent" is an affinity reagent (for example, an antibody or aptamer or oligonucleotide, polysaccharides, lipids, hormones, growth factors) that is conjugated to a synthetic tag (moiety) usually through a linker group. The tag can be, but is not limited to, a polymer with covalently attached multiple chelating groups. To a greater extent, the chelating groups can have an element or multitude of elements attached to them. The sequence and order of the chelation stage depends on the tagging protocol.

The term "detect" is used in the broadest sense meaning to include both qualitative and quantitative measurements of a specific molecule. For example, qualitative and quantitative measurements of a specific antigen or biomarker with the help of a tag (for example, a tagged antibody or other tagged affinity reagent).

"Element tag" or "tag" is a chemical moiety which includes an element or multitude of elements having one or many isotopes (referred to as "tag atoms") attached to a supporting molecular structure, or that is capable of binding said element(s) or isotope(s). The element tag can also comprise the means of attaching the element tag to a molecule of interest or target molecule (for example, an analyte). Different element tags may be distinguished on the basis of the elemental composition of the tags. An element tag can contain many copies of a given isotope and can have a reproducible copy number of each isotope in each tag. An element tag is functionally distinguishable from a multitude of other element tags in the same sample because its elemental or isotopic composition is different from that of the other tags.

The term "tag atom" is the atom of the element or isotope that differentiates one element tag from another and that is detected by elemental analysis.

"A support" is a surface which has been functionalized by, for example, pyrrole-2,5-dione (maleimido), sulfonic acid anion, or p-(chloromethyl) styrene. A support, for example, may be but is not limited to, a synthetic membrane, bead (polystyrene, agarose, silica, etc), planar surface in plastic microwells, glass slides, reaction tubes, etc. as is known to those skilled in the art.

"ICP-MS" is the Inductively Coupled Plasma Mass Spectrometer—a sensitive mass spectrometry based elemental analyzer. Different ICP-MS configurations are primarily distinguished by the mass selecting technique employed and can be, for example the quadrupole or time-of-flight (ICP-TOF) or magnetic sector (high resolution ICP-MS). There are many commercially available ICP-MS models having a wide spectrum of configurations, capabilities and modifications.

A "polymer" is a substance composed of molecules characterized by the multiple repetitions of one or more species of atoms or groups of atoms (constitutional units) linked to each other in amounts sufficient to provide a set of properties that do not vary markedly with the addition or removal of one or a few constitutional units. (IUPAC definition, see E. S. White, J. Chem. Inf. Comput. Sci. 1997, 37, 171-192). A polymer molecule can be thought of in terms of its backbone, the connected link of atoms that span the length of the molecule, and the pendant groups, attached to the backbone portion of each constituent unit. The pendant groups are often chemically and functionally different from the backbone chain. Pendant groups that have a high affinity for metal ions can act as chelating groups or ligands for those ions.

"Copolymers" are polymers that consist of two or more chemically different constituent units. A "linear polymer" is a polymer characterized by a linear sequence of constituent units. A "block copolymer" is a linear polymer with sequences of constituent units of a common type, joined to sequences of constituent units of a different type. A "branched polymer" is a polymer in which additional polymer chains (the branches) issue from the backbone of the polymer. One commonly refers to the longest linear sequence as the "main chain". A branched polymer in which the chemical composition of the constituent units of the branch chains is different than those of the main chain is called a "graft copolymer".

"Star polymers" have multiple linear polymer chains emanating from a common constituent unit or core. "Hyperbranched polymers" are multiple branched polymers in which the backbone atoms are arranged in the shape of a tree. These polymers are related to "dendrimers", which have three distinguishing architectural features: an initiator core, interior layers (generations) composed of repeating units radially attached to the initiator core, and an exterior surface of terminal functionality attached to the outermost generation. "Dendrimers" differ from hyperbranched polymers by their extraordinary symmetry, high branching, and maximized (telechelic) terminal functionality.

A "metal tagged polymer" (also a "polymeric metal tag carrier", or "metal-polymer conjugate", or "chelate-derivatized polymer") is a variety of the element tag which consists of a polymer backbone bearing at least one pendant chelating group with metal atoms attached to them. These metal tagged polymers can be, but are not limited to, linear, star, branched, or hyperbranched homopolymers or copolymers as well as block or graft copolymers.

A "metal binding pendant group" is a pendant group on the polymer that is capable of binding a metal or an isotope of a metal. It can also be referred to as a ligand.

An "attachment (linker) group" or "linker" is a portion of a molecule that is used to couple (conjugate) two different molecules or polymers, two subunits of a molecule, or a molecule to a substrate, for example an affinity agent.

Commonly used abbreviations: NAS is N-acryloxysuccinimide; NMAS is N-methacryloxysuccinimide; DMA is N,N-dimethylacrylamide; t-BDB is the reversible addition-fragmentation chain transfer (RAFT) chain transfer agent, tert-butyl dithiobenzoate; AMBN is 2,2-azobis (2-methylbutyronitrile); DMSO is Dimethyl Sulfoxide; DOTA is 1,4,7,10-tetraazacyclododecane-1,4,7,10-tetraacetic acid; PMAA is poly(methacrylic acid); DTPA is diethylenetriamine pentaacetic acid; PDMAEMA is poly(dimethylaminoethyl methacrylate); Fmoc is 9-fluorenylmethyl carbamate; DTT is dithiothreitol; TMS is trimethylsilyl and TCEP is tri(2-carboxyethyl)phosphine.

The terms Mn, Mw and PDI (polydispersity index): Mw/Mn are used to indicate the number and average molecular weight and the polydispersity index describes the molecular weight distribution, respectively.

"Chelation" is the process of binding of a ligand, the chelant, chelator or chelating agent, to a metal ion, forming a metal complex, the chelate. In contrast to the simple monodentate ligands like $H_2O$ or $NH_3$, the polydentate chelators form multiple bonds with the metal ion.

"Transition element" means an element having one of the following atomic numbers 21-30, 39-48, 57-80 and 89-92. Transition elements include the rare earth metals, lanthanides and noble metals.

"Lanthanides" are the transition metals with atomic numbers from 57 to 71 including La, Ce, Pr, Nd, Pm, Sm, Eu, Gd, Tb, Dy, Ho, Er, Tm, Yb, Lu.

"Metal" means an element having one of the following atomic numbers 3, 4, 11-13, 19-33, 37-52, 55-84, 87-102.

SUMMARY

A class of tags optimized for elemental analysis including (but limited to) the ICP-MS application has not before been developed. Preliminary studies had to be done[1;3;4;7] using tags that are currently in use for completely different purposes. The element tags of the present invention are not those of the prior art and are specifically designed for elemental analysis. To implement elemental tagging to its fullest, the development of a new class of tags was required. Inductively Coupled Plasma Mass Spectrometry (ICP-MS) has a number of unique properties that can be harnessed to create an ideal elemental tag instrument combination. The most important advantage is the fact that a large number of heavy metals and their isotopes provide distinct signals that can be detected simultaneously. Thus many, for example greater than 50, element tags can be developed; the obtained intensity of tag elements serves as a signature of the analyte concentration in the sample. Secondly, the abundance sensitivity of ICP-MS, a measure of the overlap of signals of neighboring isotopes, is large (for example greater than $10^6$ for the quadrupole analyzer), and this ensures independence of the detection channels over a wide dynamic range. The third key property is that MS is very sensitive; detection on the order of 100 molecules of a given antigen per cell may be feasible, and largely independent of the order of multiplex, a substantial improvement over current fluorescence cytometer instruments. Finally, ICP-MS as a detector offers absolute quantification that is largely independent of the analyte molecular form or sample matrix. There is a definite need to integrate these key properties of elemental analysis with bio-analytical methodology. Here, we provide a novel design of the element tags, which ensures dramatically higher multiplex capability and sensitivity of bio-assays.

The new class of polymer based element tags is suitable for determination using conventional ICP-MS instruments in the instance that an average assay over a sample ensemble (i.e., bulk assay) is desired. For example, where a tissue is sufficiently homogeneous, or the diagnostic allows for averaging over the biopsy, the sample may be stained with the metal-tagged affinity reagents and, following washing, may be acidified to lyse the cells of the tissue and provide a homogeneous solution that can be analyzed according to long-standing standard ICP-MS protocols. The bulk assay protocol still allows for massively multiplexed assay, with detection limits for each marker comparable to individual radio-immunoassay. Cell biologists might view this as a quantitative high-throughput analog of Western blotting.

The new class of polymer based element tags is suitable for determination using a novel flowcytometry ICP-MS based instrument[8] and provide up to 50 or more distinguishable reporter tags for immunological assays that enable the simultaneous determination (massively multiplexed) of many biomarkers, ultimately providing exquisite distinction and identification of diseased cells (or other cells of interest) in patient's samples in particle elemental analysis.

The new class of polymer based element tags is suitable for double labeling of affinity reagents—fluorescent label and element tag on the same affinity reagent. Previously, double labeled antibodies were used to localize specific cell types in tissue sections (fluorescent microscopy) and then identify the particular structures of cells using electron microscopy. Therefore, antibodies were labeled with fluoresceneisothiocyonate (FITC) and ferritin as an electron dense material.[9] More recently, immunoprobes that combine a fluorescent label with a small gold cluster have been prepared by covalent conjugation with Fab' fragments. These new immunoconjugates allow the collection of two complementary sets of data, from fluorescence and electron microscopy, from a single labeling experiment.[10] Another advance in reagents such as terbium-fluorescein and terbium-green fluorescent protein fluorescence resonance energy transfer pairs was achieved to study kinase reactions using Time Resolved-Fluorescence Resonance Energy Transfer (TR-FRET)[11].

The Applicant's teaching includes double labeled affinity reagents to facilitate presorting and subsequent elemental analysis of rare cells in mixed samples by ICP-MS-based flow cytometry. Cell biology requires microscopic localization of biomarkers on the cell surface or intracellularly. At the same time, quantitative information on the abundance of the markers is necessary. By covalently attaching a fluorescent label and an element tag to the same affinity reagent (for example an antibody) and using this affinity reagent, first, to localize the signal to a particular subcellular structure (membrane, nucleus, cytoplasm, cytoskeleton, etc) via fluorescent microscopy and, second, to quantify the number of bound affinity reagents by ICP-MS, will significantly increase biological understanding of processes under investigation.

An aspect of the invention is to provide an element tag comprising a polymer, wherein the polymer comprises at least one metal-binding pendant group that comprises at least one metal atom or is capable of binding at least one metal atom. The element tag can further comprise a functional group that allows the polymer to be attached to one of a linker, a spacer, or a biomolecule. The element tag can be water soluble. It can also be negatively charged. The number of metal-binding pendant groups capable of binding at least one metal atom can be between approximately 1 and 1000, and most typically between approximately 10 and 250. At least one metal atom can be bound to at least one of the metal-binding pendant groups. The polymer can have a degree of polymerization of between approximately 1 and 1000, and most typically between 10 and 250.

The polymer can be selected from the group consisting of linear polymers, copolymers, branched polymers, graft copolymers, block polymers, star polymers, and hyperbranched polymers. The backbone of the polymer can be derived from substituted polyacrylamide, polymethacrylate, or polymethacrylamide and can be a substituted derivative of a homopolymer or copolymer of acrylamides, methacrylamides, acrylate esters, methacrylate esters, acrylic acid or methacrylic acid.

The metal-binding pendant group can be attached to the polymer through an ester or through an amide. The functional group can be a thiol-reactive group. The metal atom can be a transition element or an isotope thereof, or a lanthanide or an isotope of a lanthanide. The element tag can further comprise a linker attached to the functional group of the polymer, wherein the linker is capable of covalent attachment to a biomolecule. The element tag can further comprise a spacer attached to the linker, wherein the spacer is capable of attachment to a biomolecule. The spacer can be a polyethylene glycol (PEG) spacer. The spacer can comprise a functional group that is capable of binding the spacer to the polymer via a spacer-reactive functional group on the polymer. Further the spacer can contain a functional group that is capable of binding a linker to the spacer.

The element tag described above, can be covalently attached to a biomolecule. The biomolecule can be an affinity reagent, and the affinity reagent can be an antibody.

Another aspect of the invention is to provide an element tagged affinity reagent, wherein the affinity reagent is tagged with the element tag described above, and wherein at least one of the pendant groups binds, or is capable of binding, at least one metal atom.

Another aspect of the invention is to provide a method of preparing the element tag described above, comprising: (i) providing a polymer; and (ii) covalently attaching at least one metal-binding pendant group containing at least one metal atom or capable of binding at least one metal atom to the polymer. The step of providing the polymer can comprise synthesis of the polymer wherein the synthesis is selected from the group consisting of reversible addition fragmentation polymerization (RAFT), atom transfer radical polymerization (ATRP) and anionic polymerization. The step of providing the polymer can comprise synthesis of the polymer from compounds selected from the group consisting of N-alkyl acrylamides, N,N-dialkyl acrylamides, N-aryl acrylamides, N-alkyl methacrylamides, N,N-dialkyl methacrylamides, N-aryl methacrylamides, methacrylate esters, acrylate esters and functional equivalents thereof. The metal-binding pendant group that is capable of binding at least one metal atom can comprise a diethylenetriaminepentaacetate (DTPA) ligand or a 1,4,7,10-tetraazacyclododecane-1,4,7,10-tetraacetic acid (DOTA) ligand. The method can further comprise functionalizing the polymer, wherein the functional group is capable of covalently binding a biomolecule. The method can further comprise attaching a linker to the functional group of the polymer, wherein the linker is capable of binding a biomolecule. The method can further comprise covalently binding a biomolecule to the linker. Finally, the method can further comprise binding at least one metal atom to at least one metal-binding pendant group.

Another aspect of the invention is to provide a method of preparing the element tag described above, comprising: (i) providing a polymer comprising at least one metal-binding pendant group that contains at least one metal atom or is capable of binding at least one metal atom, and comprising a functional group that allows the polymer to covalently bind a linker; (ii) attaching a linker to the functional group of the polymer, wherein the linker is capable of binding a biomolecule; (iii) covalently binding a biomolecule to the linker; and (iv) binding at least one metal atom to at least one metal-binding pendant group. The step of binding at least one metal atom to at least one metal-binding pendant group can be performed before step (ii). The step of binding at least one metal atom to at least one metal-binding pendant group can be performed before step (iii). The step of binding at least one metal atom to at least one metal-binding pendant group can be performed after step (iii). The method can further comprise a step of attaching a spacer to the linker, wherein the spacer lies between the linker and the biomolecule and/or a step of attaching a spacer to the polymer, wherein the spacer lies between the polymer and the linker. The spacer can be added before step (ii). The spacer can be a polyethylene glycol (PEG) spacer. The spacer can contain a functional group that is capable of binding the spacer to the polymer via a spacer-reactive functional group on the polymer. The spacer can contain a functional group that is capable of binding the spacer to the linker. The method can include a step of reacting the thiol with a maleimido attachment group.

Another aspect of the invention is to provide an element tag prepared by the methods described above.

Another aspect of the invention is a method for the analysis of an analyte, comprising (i) incubating the element tagged affinity reagent described above with an analyte, wherein the affinity reagent binds with the analyte; (ii) separating unbound tagged affinity reagent from bound affinity reagent; and (iii) analyzing the element bound to the affinity reagent attached to the analyte by elemental analysis.

Another aspect of the invention is to provide a method for the multiplex analysis of two or more analytes, comprising: (i) incubating two or more differential element tagged affinity reagents described above with two or more analytes, wherein the affinity reagents bind with the analytes, to produce two or more differentially tagged analytes; (ii) separating unbound affinity reagents from bound affinity reagents; and (iii) analyzing the differential tags bound to the two or more analytes by elemental analysis.

Another aspect of the invention is to provide a method for the analysis of an analyte, comprising: (i) incubating the element tag described above with an analyte, so that the element tag binds the analyte; (ii) separating unbound tag elements from bound tag elements; and (iii) analyzing the bound tag elements by elemental analysis.

The affinity reagent of any of the above methods can further labeled with a fluorescent label. The analyte can be located within or on a cell, for example a diseased cell, and further a leukemia cell. The step of analysis can comprise bulk analysis, wherein the atomic composition is averaged over an entire volume of a sample, and/or analysis of single particles. The particles can be cells.

The methods described above can be done by elemental analysis by ICP-MS or by a mass spectrometer based flow cytometer.

Another aspect of the invention is to provide a kit for the preparation of the element tag described above, comprising at least one of the following: a polymer comprising at least one metal-binding pendant group which comprises at least one metal atom or is capable of binding at least one metal atom and further comprising a functional group that allows the polymer to be attached to one of a linker, a spacer, or a biomolecule, a metal solution, reagents for the attachment of the linker, spacer or biomolecule to the polymer, reagents for attachment of a functional group to the linker or the spacer, reagents for attachment of a metal to the polymer, affinity reagents including antibodies, buffers, instructions for preparing the element tag, instructions for attaching the element tag to an affinity reagent, and instructions for attaching a metal to the element tag.

Another aspect of the invention is to provide a kit for the analysis of analytes according to the methods described above comprising at least one of the following: a polymer comprising at least one metal-binding pendant group which contains at least one metal atom or is capable of binding at least one metal atom and further comprising a functional group that allows the polymer to be attached to one of a linker, a spacer, or a biomolecule, a metal solution, reagents for the attachment of the linker, spacer or biomolecule to the polymer, reagents for attachment of a functional group to the linker or the spacer, reagents for attachment of a metal to the polymer, affinity reagents including antibodies, buffers, instructions for preparing the element tag, instructions for attaching the element tag to an affinity reagent, instructions for attaching a metal to the element tag. and instructions for using the element tags for the analysis of analytes by elemental analysis.

The polymer for any of the above kits can be selected from the group consisting of homopolymers or copolymers of acrylamides, methacrylamides, acrylate esters, methacrylate esters, acrylic acid and methacrylic acid. The reagents can include at least one of the following: TCEP (tri(2-carboxyethyl)phosphine), Ligand-Polymer-Linker-Spacer Conjugate, phosphate buffer, TBS (tris-buffered saline), EDTA (Diaminoethanetetraacetic acid), ammonium acetate buffer, antibodies, metal salt solution, lanthanide salt solution, blocker buffers, washing buffers, FBS (fetal bovine serum), DMEM (Dulbecco's Modified Eagle's Medium), BSA (bovine serum albumin), dithiothreitol, bismaleimide, and DMF (dimethylformamide). The polymer can be attached to a linker or it can be attached to a linker and a spacer.

These and other features of the applicant's teachings are set forth herein.

BRIEF DESCRIPTION OF THE FIGURES

The invention is illustrated in the figures of the accompanying drawings, which are meant to be exemplary and not limiting, and in which like references are intended to refer to like or corresponding parts.

FIG. 8. Experimental conditions and molecular weight data for random copolymers of DMA and NAS in dioxane at 80° C.

DESCRIPTION OF THE VARIOUS EMBODIMENTS

The overall requirements for an element tag are less stringent than those for a fluorescent tag[12] since the chemical nature of an element is not important for its detection by elemental analysis. The tag should contain a reproducible and, preferably, large number of atoms of a given element or isotope composition. The tag can comprise one element or isotope, or consist of a composition of more than one element or isotope. It can also include a natural mixture of isotopes. Further, it is possible that the element tag can comprise one pendant group comprising a certain metal or isotope and a second pendant group comprising another metal or isotope. Reproducibility in the number of identical atoms incorporated is a basis for quantitative analysis, and an increase in the number of those atoms improves the sensitivity linearly. Another key attribute is resistance to leaching, which distinguishes this invention from the DELFIA products. Mobility of the chelated metal is required in the DELFIA products (DELFIA® Assays and Reagents, PerkinElmer, USA). The tag atoms can be any atoms of an element or isotope that differentiate the tag from other atoms in the sample including from other tag atoms associated with differentiated element tags. Typically, the tag atoms will be metals, in particular transition elements, and most typically lanthanides.

Figure 1:
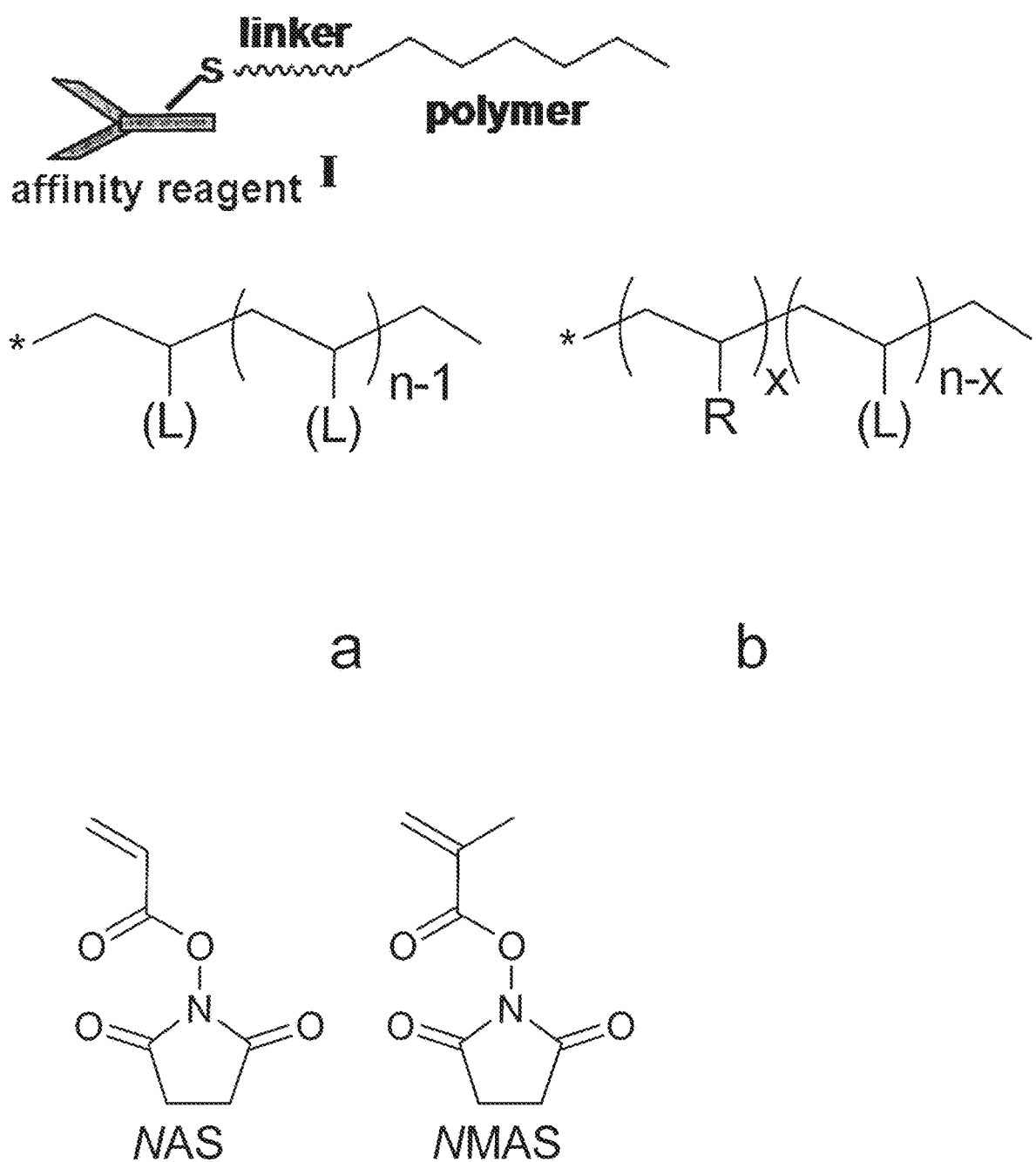
FIG. 1. Schematic views of the element tags for the detection of biomolecules which according to the invention have the general structure I. Proposed polymeric metal chelates: R=organic group, L=Metal ligand. In structure "a" each repeat unit of the polymer bears the liganded Ln3+, denoted by (L). In structure "b", a fraction of the repeat units have an organic group R according to the invention. Asterisk (*) represents the initiated end of the polymer NAS is schematic view of N-acryloxysuccinimide. NMAS is schematic view of N-methacryloxysuccinimide.

The tags to be employed for the detection of analytes have the general structure I of FIG. 1.

The polymer can be any polymer as is known to those skilled in the art. Examples of polymers are shown in FIGS. 1 through 4. Further, the polymer backbone can be derived from a substituted polyacrylamide, polymethacrylate, or polymethacrylamide. Further still, the backbone of the polymer can be a substituted derivative of a homopolymer or copolymer of acrylamides, methacrylamides, acrylate esters, methacrylate esters, acrylic acid or methacrylic acid. The polymer can be synthesized by many methods as are known to those skilled in the art. For example, the synthesis can be accomplished with compounds such as N-alkyl acrylamides, N,N-dialkyl acrylamides, N-aryl acrylamides, N-alkyl methacrylamides, N,N-dialkyl methacrylamides, N-aryl methacrylamides, methacrylate esters, acrylate esters and functional equivalents thereof.

Figure 2:
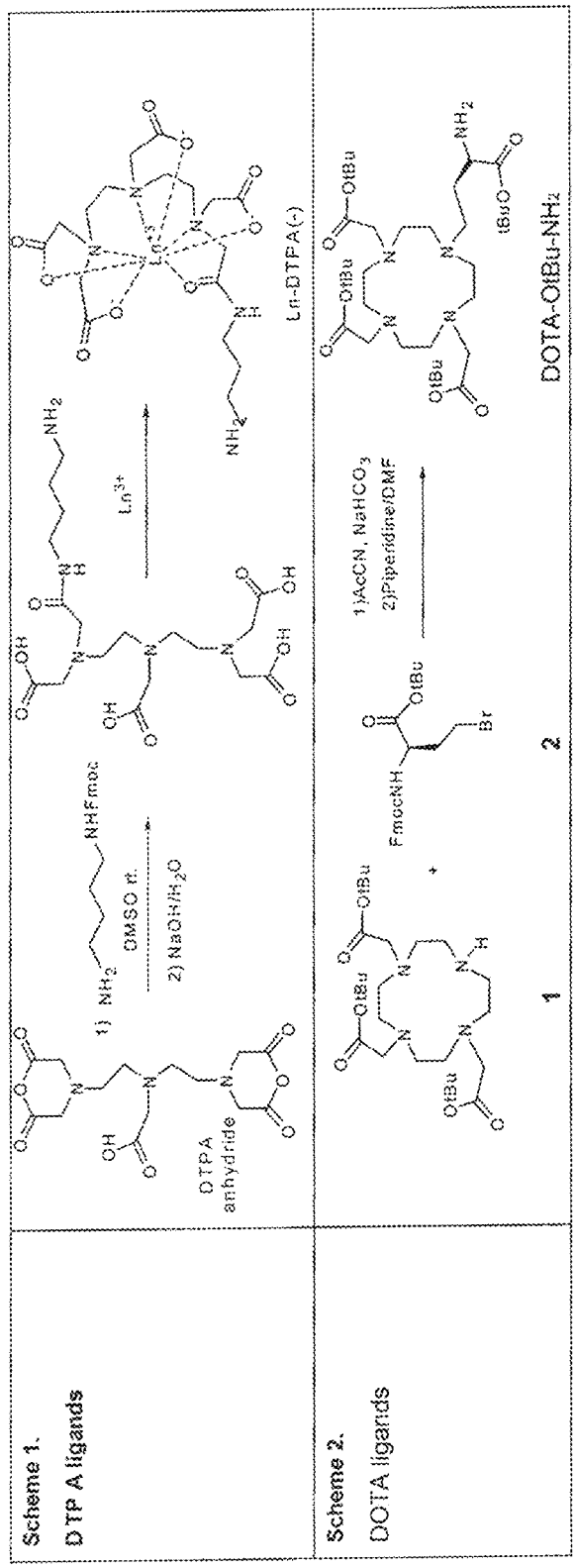
FIG. 2. Schematic views of an example of the synthesis of functional ligands that can be used to attach the element/metal "L" to the polymer.
Figure 3:
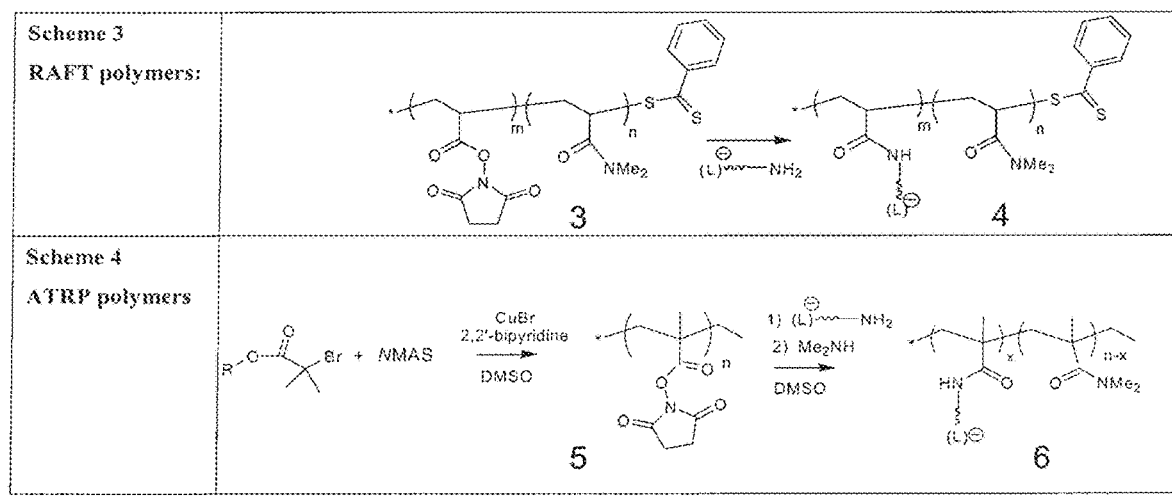
FIG. 3. Schematic views of attaching ligands (pending groups) to the RAFT polymers (Scheme 3) and ATRP polymers (Scheme 4).
Figure 4:
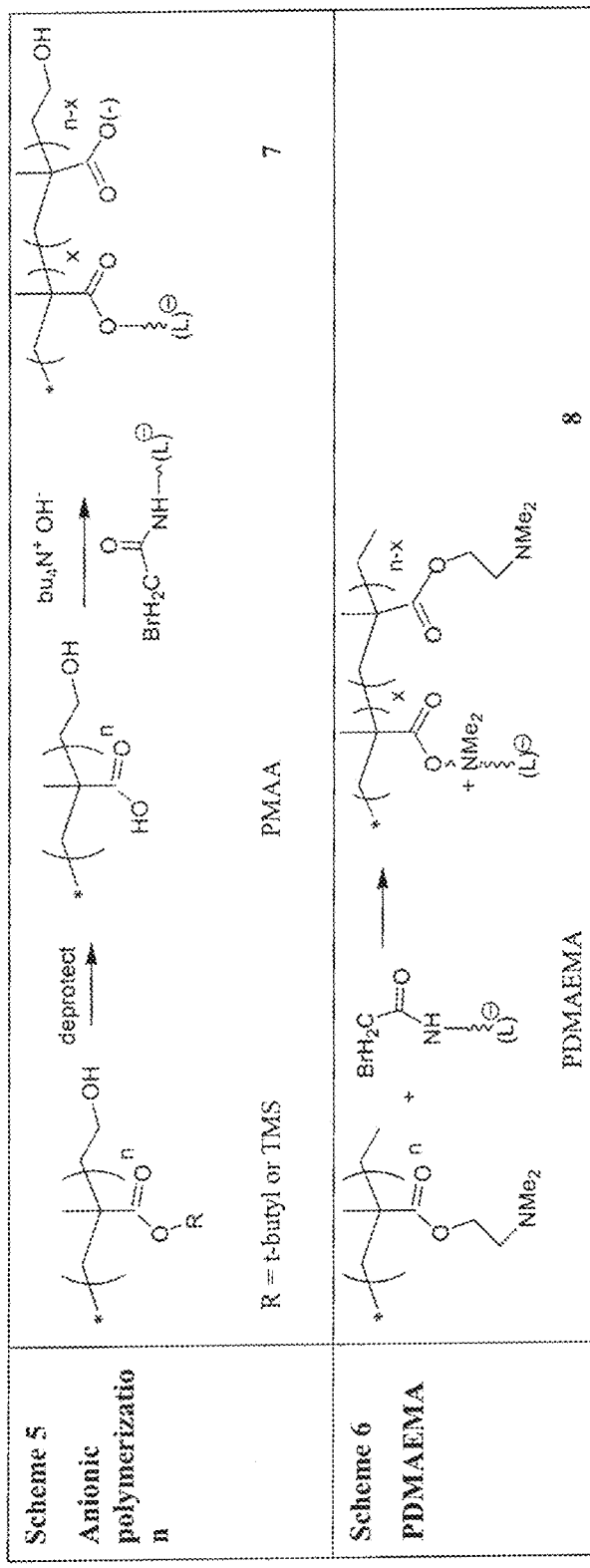
FIG. 4. Schematic views of attaching ligands (pending groups) to polymers produced by anionic polymerization (Scheme 5) and PDMAEMA (Scheme 6).

The ligand or pendant group can be any ligand as is known to those skilled in the art. Examples of ligands are shown in FIGS. 2 through 4.

Figure 5:
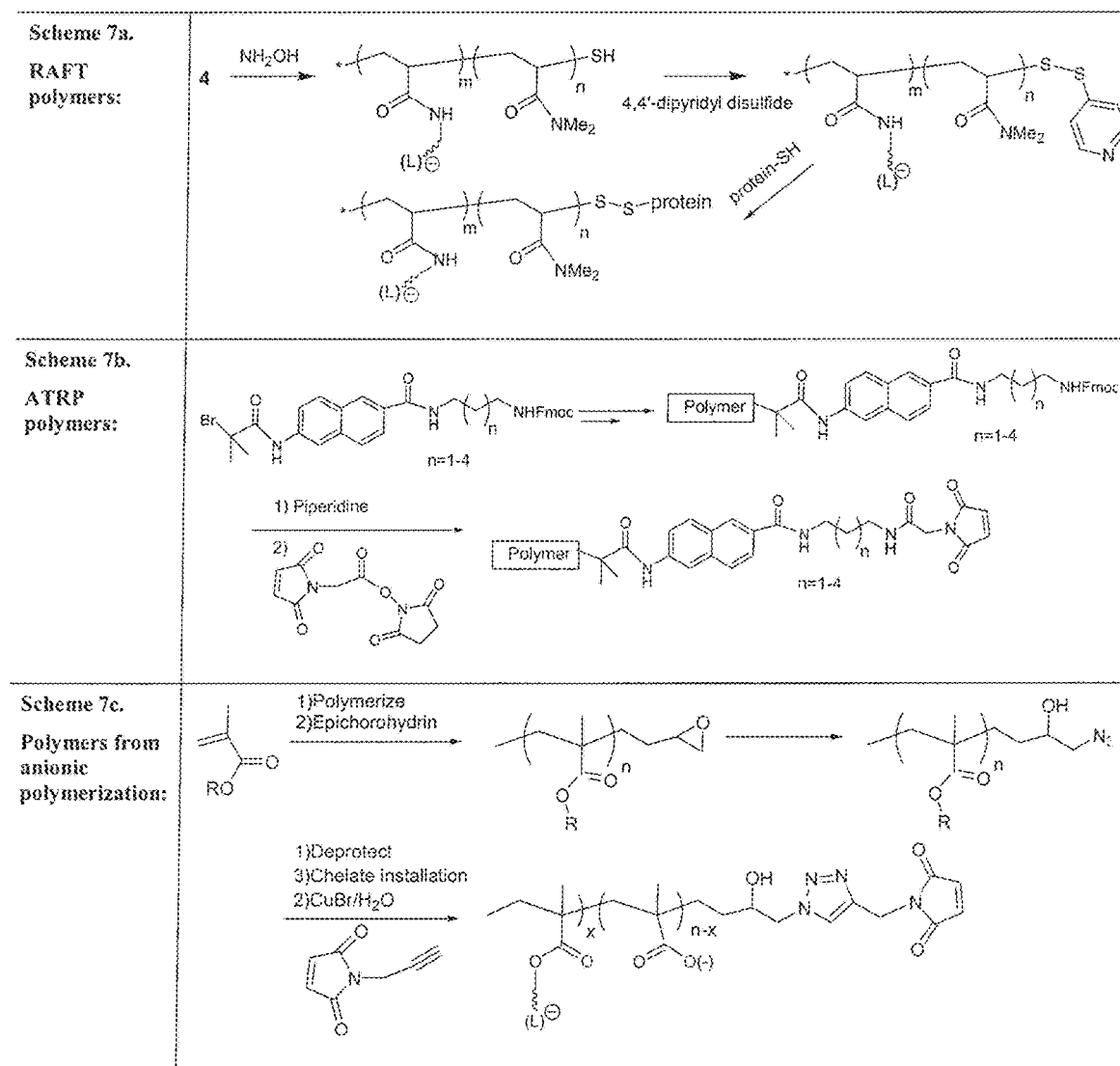
FIG. 5. Schematic views of attachment of the coupling group (the linker) to the RAFT polymers (Scheme 7a), ATRP polymers (Scheme 7b), and polymers produced by anionic polymerization (Scheme 7c).
Figure 6:
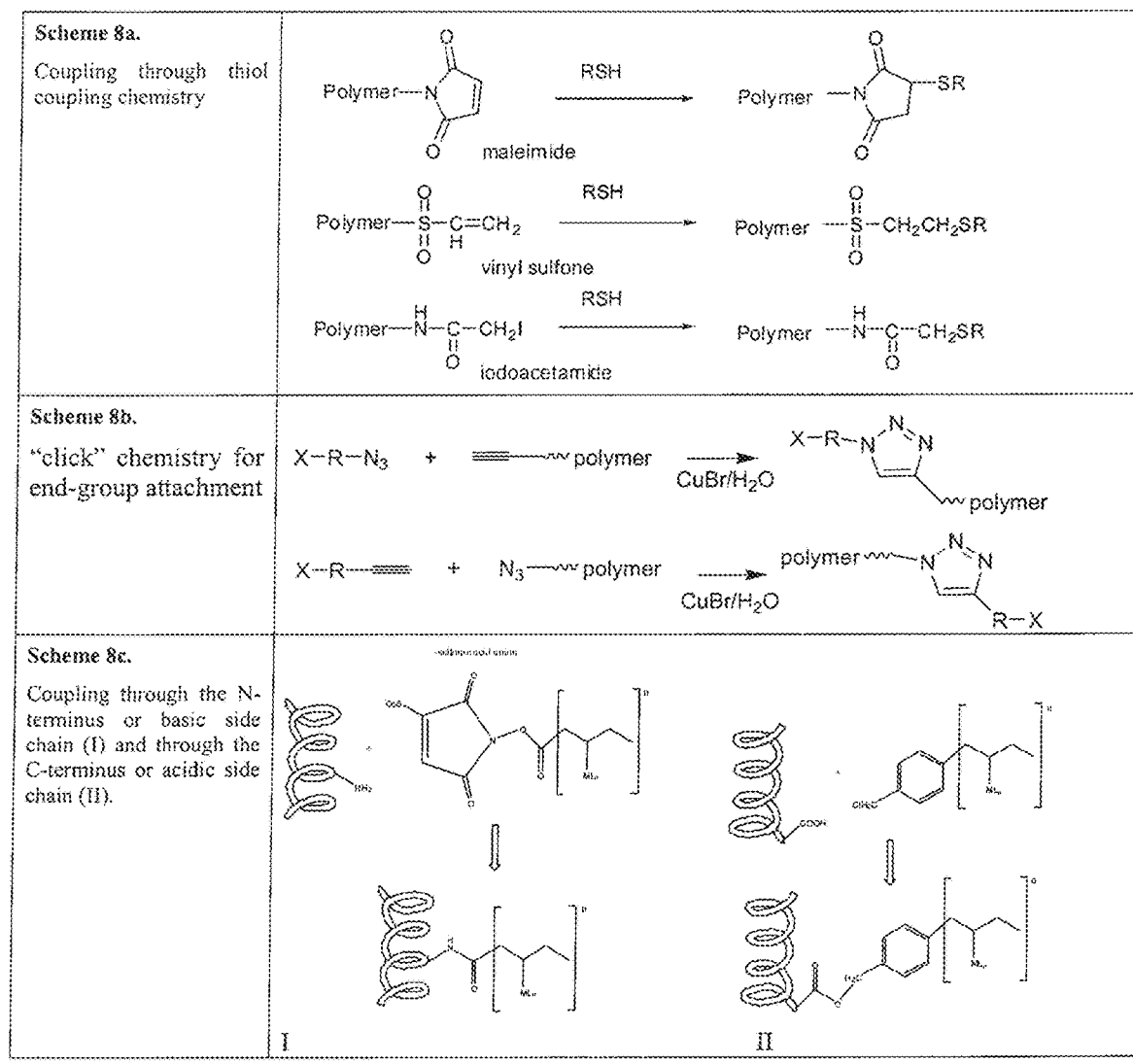
FIG. 6. Schematic views of alternative examples of coupling chemistry according to the invention. In scheme 8b, the term "end-group" is used to refer to the coupling group.

The linker can be any linker as is known to those skilled in the art. Examples of linkers are shown in FIGS. 5 and 6. The linker is optional.

The spacer is optional. Examples of spacers include PEG block spacers, and others known to those skilled in the art.

The invention involves primarily but not exclusively the following aspects:

(i) Polymeric metal tag carrier synthesis. Functionally, the metal tagged polymer is stable under typical assay conditions, which includes very low kinetic lability of bound metals and rate of exchange of metals between polymers;

(ii) Synthesis and characterization of the attachment (linker) group in combination with polymeric metal tag carrier;

(iii) Synthesis of tagged affinity reagent, which functionally includes an attachment (linker) group in combination with the polymeric metal tag carrier. The tagged affinity reagent can be a tagged antibody or other tagged affinity reagent; and (iv) Method of employing the affinity reagents as multiplexing tools.

More generally the invention involves synthesis and testing of metal-containing tags for labeling of bio-organic molecules, including affinity reagents such as antibodies. Specifically designed for elemental analysis, such a tag would typically be: (i) water soluble, (ii) non-toxic, (iii) easily separated from a tagged material by known chromatographic, centrifugation, filtration or dialysis methods; and, in addition, can have three or four moieties: the attachment group (linker), possibly a spacer (for example, a PEG spacer), the polymer skeleton (carrier), and the tag atoms (as many tag atoms (of the same metal or isotope, or of a different metal and/or isotope) as possible). For different elemental analyzers the characteristics of the element tag can be similar.

Although an embodiment of the invention using antibodies as the affinity reagent is exemplified, it is to be understood that other affinity reagents can be used and are within the scope of the invention.

Polymer carrier: An important aspect of the invention is the synthesis of a polymer, to which a large number of tag atoms can be attached. Typically the tag atoms are metal atoms. The polymer can be water soluble This moiety is not limited by chemical content. However, it simplifies analysis if the skeleton has a relatively reproducible size (for example, length, number of tag atoms, reproducible dendrimer character, etc.). The requirements for stability, solubility, and non-toxicity are also taken into consideration. Thus, the preparation and characterization of a functional water-soluble polymer by a synthetic strategy that places many functional groups along the backbone plus a different group at one end that can be used to attach the polymer via a linker to a biomolecule (for example, an affinity reagent) is part of this invention.

The tags to be employed for the detection of analytes have the general structure I of FIG. 1. The signal to be detected will be that of the polymer, which will contain between approximately 1 to 1000 (or more) atoms of an element (for example, lanthanide (Ln) atoms) as part of its structure. A flexible linker/spacer at one end of the polymer may contain a thiol-reactive functional group such as a maleimide, and through this group can be linked to an affinity reagent (for example an antibody) for the specific target analyte. Variations include the attachment to primary amines of biomolecules or other methods of attachment known to persons skilled in the art. Examples of the selection of functional groups for the linker arm can be taken from the literature on PEGylated antibodies, reviewed recently by Chapman[13]. The polymers as carriers of the metal-atom tags have a similar number of backbone atoms as those of the PEG polymers that have been attached to various antibodies without loss of binding affinities. For example a PEG2000 (2 KDa) has a mean degree of polymerization of 45 corresponding to 140 backbone atoms, and PEG5000 has 340 backbone atoms. To put these tags in perspective, the average size of an IgG antibody from the end of the Fc to the Fab is approximately 11 nm[14]. The radius of gyration of the polymer constructs should be as small as possible, somewhere between approximately 2 nM and 11 nM.

In one embodiment, the invention involves polymers containing the Ln3+ atoms as substituents of the pendant groups and their synthesis. In structure "a" of FIG. 1, each repeat unit of the polymer bears the liganded Ln3+, the group being denoted by (L). It is neither likely nor required that each pendant group bear an (L) substituent. In structure b of FIG. 1, a fraction of the repeat units have an organic group R. In these structures, the asterisk (*) represents the initiated end of the polymer. The following factors are considered: 1) The polymer can be water soluble. Because of their hydrolytic stability, N-alkyl acrylamides, N-alkyl methacrylamides, and methacrylate esters or functional equivalents can be used. 2) A degree of polymerization (DP) of approximately 1 to 1000 (1 to 2000 backbone atoms) encompasses most of the polymers of interest. Larger polymers are in the scope of the invention with the same functionality and are possible as would be understood by practitioners skilled in the art. Typically the degree of polymerization will be between 10 and 250. 3) The polymers may be amenable to synthesis by a route that leads to a relatively narrow polydispersity. The polymer may be synthesized by atom transfer radical polymerization (ATRP) or reversible addition-fragmentation (RAFT) polymerization, which should lead to values of Mw/Mn in the range of 1.1 to 1.2. An alternative strategy involving anionic polymerization, where polymers with Mw/Mn of approximately 1.02 to 1.05 are obtainable. Both methods permit control over end groups, through a choice of initiating or terminating agents. This allows synthesizing polymers to which the linker can be attached. 4) A strategy of preparing polymers containing functional pendant groups in the repeat unit to which the liganded transition metal unit (for example a Ln unit) can be attached in a later step can be adopted. This embodiment has several advantages. It avoids complications that might arise from carrying out polymerizations of ligand-containing monomers. In addition, the polymer backbone is a known one that can be adapted for most if not all of the Ln-containing polymers. Thus the polymers may have a common mean chain length and chain-length distribution. 5) The target polymers of type "a" may either be negatively charged polyelectrolytes or have zwitterionic pendant groups. To minimize charge repulsion between pendant groups, the target ligands for (Ln3+) should confer a net charge of −1 on the chelate. For type "b" polymers, the R groups are for the most part uncharged, although in one example, the inventors teach a polymer in which the small fraction x of R groups will have a positive charge. Finally, various chemistries are well known that enable the attachment of the linker group with its thiol reactive group to the polymer. A number of pendant groups can be added to the polymer. Practically, the number can be between 1 and 1000, and more typically between 10 and 250. The metal-binding pendant group can be attached to the polymer by methods known to those skilled in the art, for example, the pendant group may be attached through an ester or through an amide.

Examples for the synthesis of functional ligands that are used to attach (L) to the polymer are shown in FIG. 2 (Schemes 1 and 2). The examples are exemplary and are not intended to limit the scope of the invention.

Chelate (tag atom) choice and synthesis: The use of the lanthanides is established here as feasible, however, similar results can be achieved for different elements. Across the series of lanthanides very similar coordination chemistry is observed. All the lanthanides favor the +3 oxidation state and preferentially coordinate with hard oxygen ligands. Lanthanides do not exhibit defined coordination geometries and vary in coordination number between 7 and 10 across the series. Thus, the same chelate-derivatized polymer can be used for all the Ln metals, which facilitates production of tags containing different lanthanides used in multiplexing assays[15]. Different embodiments utilizing different metals can be obtained using similar considerations related to their chemical nature. Numerous Ln complexes have been developed for use as radiopharmaceuticals and imaging agents[16]. But the art does not disclose metal atoms attached to pendant groups on the polymer backbone. The multidentate chelates developed for these applications form thermodynamically stable and kinetically inert Ln complexes, important for minimizing the toxicity of free lanthanides in vivo. Incorporating these optimized lanthanide chelates, as pendant groups on polymeric structures, appears to be described here for the first time.

As examples, two ligand frameworks as functional examples of covalently linked chelates on the polymeric backbone are described. The selection criteria for this embodiment include known syntheses, heptadentate or octadentate coordination to promote kinetic stability against metal ion dissociation, a pendant primary amine functional group for attachment of the chelate to the polymer, and a net charge of −1 for the liganded chelate. Diethylenetriamine-pentaacetate (DTPA), an acyclic chelator can be readily derivatized as an amine functionalized ligand (Scheme 1, FIG. 2). Coupling a monoprotected diamine with the commercially available DTPA anhydride, followed by deprotection provides a candidate ligand to be coupled to the polymeric active ester. The net charge of the compound once complexed to lanthanide is −1. The facile synthesis of this chelator makes it an attractive starting point for optimizing the polymeric backbone with attached chelators.

DTPA ligands are inherently more kinetically labile than the macrocyclic ligand based on the cyclen framework. The macrocyclic nature of the cyclen-based ligands preorganizes the metal binding site, leading to greater thermodynamic and kinetic stability. These chelates are known to be stable in vivo for days[17]. Reaction of commercially available tritert-butylmethylcyclen (Macrocylics) with the readily available homoserine derivative provides an orthogonally protected DOTA derivative (Scheme 2, FIG. 2)[18]. The Fmoc protecting group can be removed to access the amine and make it available to couple with the polymeric backbone. In some instances it may be necessary to employ a spacer between the DOTA chelate and the polymer. A variety of selectively protected amino acids of different lengths is commercially available and can be readily coupled and deprotected to form linkers. The lanthanide complex of this chelate will carry a net −1 charge. Based on functionality, these Ln chelates with the reactive —$NH_2$ group are referred to as (L)-$NH_2$.

Polymer synthesis and chelate attachment: Herein below, the synthesis of candidate polymers, the attachment of functional chelates to the polymer backbone, and the characterization of the metal containing polymers are described. These are intended to be examples, and not to limit the scope of the claims. Other examples can be used as is known to those skilled in the art.

Figure 15:
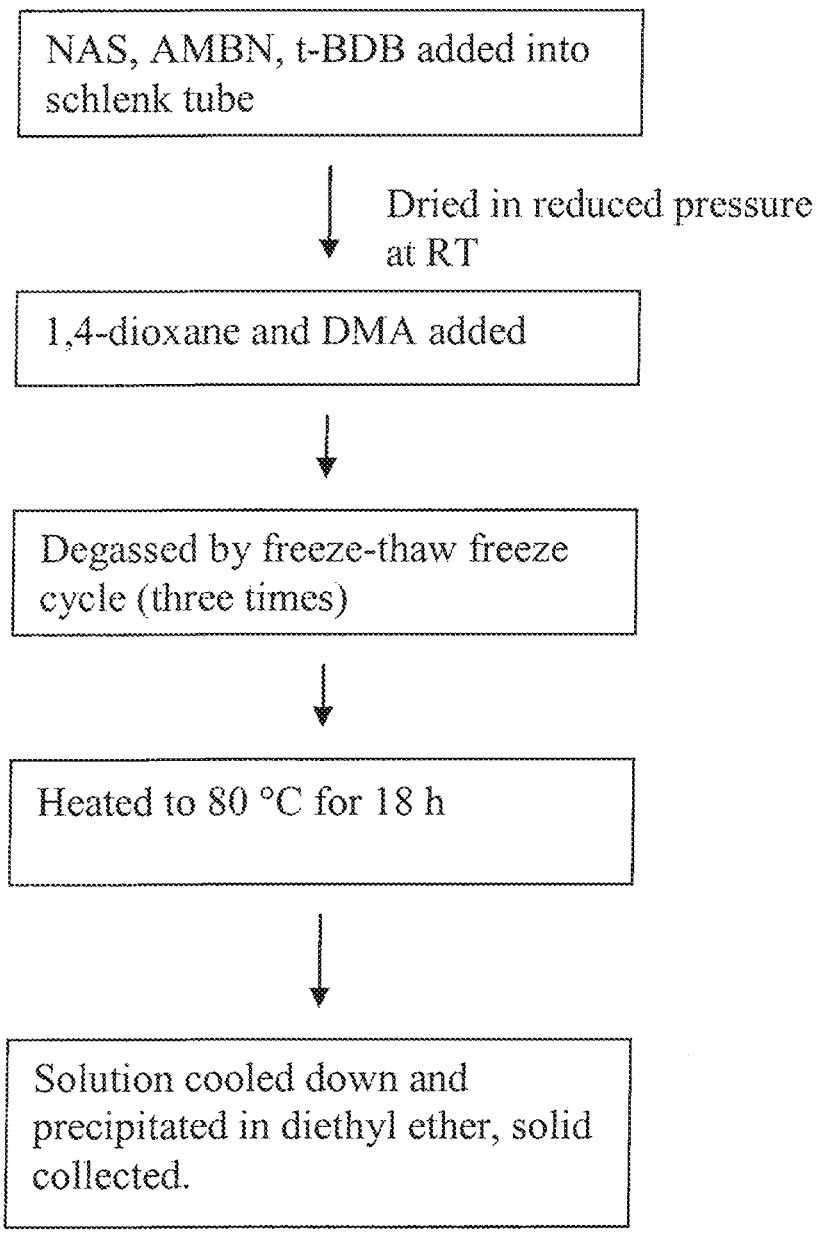
FIG. 15 is a flow Chart I of RAFT polymerization procedure.

Random copolymer poly(DMA-co-NAS): A recent report[19] describes the synthesis of a 75/25 mole ratio random copolymer (3, FIG. 3) of N-acryloxysuccinimide (NAS) with N,N-dimethyl acrylamide (DMA) by RAFT with high conversion, excellent molar mass control in the range of 5000 to 130,000, and with Mw/Mn≈1.1. In this embodiment (Scheme 3, FIG. 3), the active NHS ester of 3, FIG. 3 is reacted with a liganded lanthanide (L) bearing a reactive amino group to yield the copolymer 4, FIG. 3. FIG. 15 is a flow chart showing the steps involved in RAFT polymerization.

Poly(NMAS): Yet another approach has been reported by Müller[20] and used to attach drug conjugates to the polymer backbone. In this approach, Müller polymerized NMAS by ATRP (Scheme 4, FIG. 3), obtaining polymers with a mean molar mass ranging from 12 to 40 KDa with Mw/Mn of approximately 1.1. In their experiments, limiting amounts of various drugs or drug-mimics bearing a spacer and a primary amine were reacted with the NHS ester groups of 5, FIG. 3, and then the remaining sites were reacted with excess $Me_2NH$. Their initiator was the hydroxyethyl ester of bromoisobutyric acid; thus the polymer chains all had a primary alcohol as an end group. Here samples of 5, FIG. 3, are reacted with excess (L)-$NH_2$, maximizing the number of (L) groups that can be attached to the polymer.

Poly(MAA): Another aspect of the Applicant's teaching is related to specific functional advantages of polymer tags with a very narrow molar mass distribution. Polymethacrylic acid (PMAA) can be prepared by anionic polymerization of its t-butyl or trimethylsilyl (TMS) ester. If the reaction is terminated with ethylene oxide prior to ester hydrolysis (FIG. 4), the polymer will bear a —$CH_2CH_2$—OH as a functional end group. A route for attaching (L) to the polymer involves reacting the tetrabutylammonium carboxylate salt of the polymer with the bromoacetamide derivative of (L)-$NH_2$ (Scheme 5, FIG. 4).

Poly(DMAEMA): Recently, samples of poly(dimethylaminoethyl methacrylate) (PDMAEMA) were prepared by ATRP[21]. This is a well-known polymer that is conveniently prepared with mean Mn values ranging from 2 to 35 KDa with Mw/Mn of approximately 1.2 This polymer can also be synthesized by anionic polymerization with a narrower size distribution[22]. This polymer can be reacted with the bromoacetamide derivative of (L)-NH2. This yields a zwitterionic polymer 8, Scheme 6, FIG. 4, which has suitable water solubility. The unreacted dimethylaminoethyl groups will be protonated at neutral pH and contribute a small positive charge to the polymer.

Spacers: A potential source of interference between a metal-bearing polymer tag and affinity reagent activity is the close proximity of the bulky polymer when attached to the affinity reagent. Spacers, for example, PEG spacers, can be situated between the linker and the polymer or between the polymer and the linker. Methods for the addition of spacers is known to those skilled in the art.

The spacer can also be an integral part of the polymer backbone to help mitigate this problem. In the applicant's teaching, the syntheses (for example see Schemes 4-6, FIGS. 3 and 4) can be modified to create PEG block copolymers. The PEG portion of the block copolymer serves as a PEG spacer, and the synthetic strategies make it possible to vary the PEG spacer length as needed in response to bioassay results that indicate problems with binding efficiency or sensitivity. The spacer can be any spacer as is known to those skilled in the art. For example, it can be a minimal spacer as shown in Scheme 12 and compound 12. This specific enactment seems to be novel as we are not aware of its prior application.

End-group control and coupling chemistry: According to the Chapman review on PEGylated antibodies[13], approaches to PEG attachment via reaction with the free amino group of the lysine were successful, but the PEGylated antibodies obtained exhibited reduced antigen binding efficiency. It appears that the random nature of the chemical reaction to the various lysine groups in the antibody led to PEG attachment at sites that interfered with binding. A more benign result was obtained for the case in which the PEG chain was attached specifically to a single cysteine in the FC fragment that was introduced into the antibody through site-specific mutation. Here reduction of a disulfide bond within the FC fragment of the antibody, followed by covalent attachment of the polymers to one or both of the —SH groups formed is described. Thus a thiol reactive group may be used at one terminus of the polymers.

RAFT polymers: The thiobenzoate end group of RAFT polymers is conveniently converted to a terminal —SH group. This chemistry is shown in scheme 7a, FIG. 5, for polymer 4, FIG. 3. Numerous methods are known, to those skilled in the art, for crosslinking thiols, in analogy with reactions described for —SH terminated polyethylene glycol (PEG-SH)[23], and allow the attachment of the polymer via the mixed disulfide to the free —SH of an antibody or other affinity reagent (denoted as "protein-SH"). Alternatively, bismaleimide derivatives are commercially available and alkylation of the polymer with these reagents followed by GPC (Gel Permeation Chromatography) purification and reaction with the free thiol of the antibody or other affinity reagent provides the desired conjugate[24].

ATRP polymers: Polymers of the structure 5, FIG. 3, reported by the Müller group[25] have a terminal —CH2CH2—OH group. A different initiator for the polymerization reaction is described here. 2,6-napthalene derivatives are readily available and will provide an orthogonally protected amine. After deprotection, reaction of the amine with a bifunctional NHS-maleimide, the thiol-amine crosslinking agent will provide the polymeric labeling agent for antibody conjugation. This initiator also provides a convenient chromophore for quantification of the polymer. This also shown in scheme 7b in FIG. 5.

Anionic Polymerization (Scheme 5, FIG. 4): Anionic polymerizations can often be terminated by reaction with functional electrophiles to introduce an end group to the polymer[26]. Enolates react effectively with allylic and benzylic halides[27]. Quenching styrene polymerization with epichlorohydrin has been shown to be problematic[28]. Conditions for quenching the enolate end of a living poly(t-butyl methacrylate) to yield the terminal epoxide are described here. While glycidyl methacrylate can be polymerized anionically at low temperature in the presence of LiCI, which makes the propagating anion less nucleophilic[29], it is expected that the enolate of t-butyl methacrylate should ring-open an epoxy group at higher temperature[30]. Opening of the epoxide with azide provides an orthogonal functional group stable under conditions of ester hydrolysis. Treatment of azides with an alkyne in the presence of Cu(I) salts yields triazoles in high yield[31]. By using this coupling reaction a thiol reactive maleimide is installed at the terminus of the polymer. This is also shown in scheme 7c in FIG. 5.

Attachment (linker) groups: The attachment group provides a covalent bond between bioorganic (proteins, peptides, oligonucleotides) molecules, for example affinity reagents, and the element tag. For example, the linkage can be effected via thiols using a maleimido attachment group; through the N-terminus or basic side chain (lysine, arginine, histidine) (see Scheme 8c, FIG. 6), through the C-terminus or acidic side chain (aspartic acid, glutamic acid) using p-(chloromethyl)styrene (see Scheme 8c, FIG. 6), or via oxidation of the sugar moiety on the antibody or other affinity reagent and coupling via a hydrazine group. One may take advantage of thiol groups created by reduction of the disulfide bond in the FC fragment of the antibody. This combination "bioorganic molecule—attachment group—element tag" is thought to be described here for the first time.

Functional example of coupling chemistry: There are four main coupling chemistries commonly used to attach polymers (such as PEG) to the free thiols of proteins. The advantages and disadvantages of each of these reactions have recently been reviewed[32]. One approach involves disulfide exchange as shown in Scheme 7a, FIG. 5. Three other common reactions involve addition of —SH to a maleimide or a vinyl sulfone and the displacement of iodide from an iodoacetamide (Schemes 8a-c, FIG. 6). To avoid the slow hydrolysis in water that is typical of maleimide and iodo-acetamide groups, a strategy in which the thiol-reactive agent is added to the end of the (L)-bearing polymer just prior to tagging of the affinity reagent is possible. This strategy takes advantage of the "click" chemistry developed recently by Sharpless[33] (Scheme 8b, FIG. 6) involving the 1,3-dipolar addition of azides to acetylenes, a reaction that Sharpless has shown to occur under mild conditions with quantitative yield. To introduce the acetylene unit on the end of polymers bearing a terminal —$NH_2$ group, they are reacted with an active ester derivative of 4-pentynoic acid. The polymer is then set up for a reaction with a derivative of the form X—R—N3, where R is the spacer and X represents the thiol-reactive group.

Coupling of polymer to an antibody or other affinity reagent: As an example, reduction of disulfide bonds in an antibody or other affinity reagent can be performed using immobilized trialkylphosphine TCEP (Tris[2-carboxyethyl] phosphine hydrochloride) covalently linked to a beaded agarose support (Pierce). TCEP is known to be an efficient reductant of alkyl disulfides over a wide range of pH and does not interfere with commonly used sulfhydryl-reactive reagents such as maleimide cross-linkers. The use of beads permits recovery of the reduced antibody or other affinity reagent by simple centrifugation from the reducing agent with subsequent separation from the beads.

Purification of polymer modified antibodies: Due to the large size of the IgG antibodies (150 KDa) one option is to separate the excess metallated labeling polymer (20-40 KDa) from the antibody using gel filtration chromatography. Alternatively, Protein A and Protein G have been used to purify antibodies.

As is known to those skilled in the art, the element or metal atoms can be added to the polymer tag at different steps during the production of the tagged biomolecule. It is beneficial to add the element (metal) of the tag after conjugation of the antibody or other affinity reagent with the ligand-polymer. This strategy has several advantages: i) conversion of antibody-ligand-polymer conjugate into antibody-metal-polymer conjugate can be done directly before bio-assay; ii) the multitude of affinity molecules can be tagged with the same ligand-polymer solution under the same conditions. The choice of metal (or isotope) to use can be determined directly before the multiplexed experiment by the reagent user significantly increasing experimental flexibility; iii) decoupling of both tagging stages allows series of important independent control experiments in which the same antibody can be tagged with different metals; iv) selection of the internal standards is unhindered, and the relative sensitivity of the elemental analyzer can be effectively controlled.

The order of steps for the synthesis of the tagged biomolecule can take many forms. Three examples are provided below, but it is to be understood that other orders of steps are possible:

| A | B | C |
|---|---|---|
| Synthesize polymer | Synthesize polymer | Synthesize polymer |
| Bind metal to polymer | Bind linker to polymer | Bind linker to polymer |
| Bind linker to polymer | Bind metal to polymer | Bind linker to antibody |
| Bind linker to antibody | Bind linker to antibody | Bind metal to polymer |

Further, the linker can be attached to the biomolecule before the linker is attached to the polymer. Most often, the metals will be attached anytime before binding the tagged affinity reagent to the analyte. It is possible to add the metals after attaching the affinity reagent to the analyte, but the background is expected to be elevated because many analytes, and in particular cells, will bind metals non-specifically. It is therefore less likely to be performed successfully after binding the affinity reagent to the analyte.

Further, the polymer element tag may be attached to a biomolecule which is other than an affinity reagent. For example, the polymer element tag may be attached directly to an analyte, for example but not limited to a growth factor, cytokine or chemokine for studying kinetics of ligand-receptor interactions. Specifically, EGF (epidermal growth factor) with polymer element tag may be used as a probe to investigate EGFR (epidermal growth factor receptor) abundance on cell surface, receptor dimerization and internalization. This aspect is also within the scope of the applicant's teachings. Two or more analytes may also be analyzed in a multiplex reaction.

Aspects of the Applicant's teachings may be further understood in light of the following examples, which should not be construed as limiting the scope of the present teachings in any way.

EXAMPLES

Figure 7:
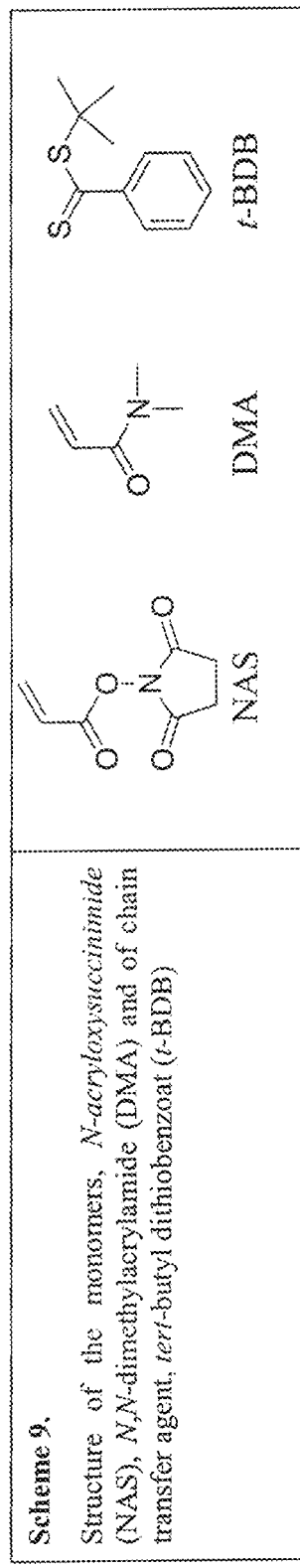
FIG. 7. Schematic views of structures of monomers.

Example 1. Synthesis of Copolymers of N,N-dimethylacrylamide and N-acryloxysuccinimide by RAFT Polymerization N,N-dimethylacrylamide (DMA) and N-acryloxysuccinimide (NAS) were copolymerized by the reversible addition-fragmentation chain transfer (RAFT) polymerization technique, to obtain random copolymer precursors with side-groups statistically grafted via the reactive NAS units[19]. The random copolymers of DMA and NAS, poly(DMA-co-NAS), were prepared using tert-butyl dithiobenzoate (t-BDB) as chain transfer agent (CTA) (Scheme 9, FIG. 7).

Preparation of tert-Butyl Dithiobenzoate (t-BDB).[34] In a 500 mL round-bottomed flask equipped with a magnetic stirrer, 150 mL of a diethyl ether solution of s-(thiobenzoyl) thioglycolic acid (0.27 g, 2.4 mmol) was added to 100 mL of an aqueous basic solution (NaOH, 1 mol $L^{-1}$) of sodium 2-methyl-2-propanethiolate (0.510 g, 2.9 mmol). This biphasic mixture was vigorously stirred at room temperature for 5 hours. Then, the purple ether phase was removed and washed twice with 500 mL of an aqueous basic solution (NaOH 1 mol $L^{-1}$) and twice with 500 mL of a 10% NaCl aqueous solution and dried over anhydrous magnesium sulfate. Purification by silica gel chromatography (Kiesegel-60) with petroleum ether/ethyl acetate (99/1:v/v) as eluent gave tert-butyl dithiobenzoate (t-BDB) as a dark purple oil (90% yield). 1H NMR (CDCL3) d (ppm): 1.69 (S, 9H, 3×CH3), 7.36 (m, 2H, meta-ArH), 7.50 (m, 1H, para-ArH) and 7.88 (m, 2H, ortho-ArH).

Preparation of N-acryloxysuccinimide (NAS).[35] N-hydroxysuccinimide (10 g, 0.086 mol) and triethylamine (13.2 g, 0.129 mol) were dissolved in chloroform (130 mL) at 0° C. Acryloyl chloride (8.6 g, 0.094 mol) was added dropwise over a period of 2 hours to the stirred reaction mixture. The reaction is described in Scheme 1, FIG. 2. After being stirred an additional 30 minutes at 0° C., the solution was washed twice with 60 mL saturated NaCl aqueous solution, dried over MgSO4, filtered and concentrated so as to get a residual volume of 30 mL. An ethyl acetate/pentane mixture (14 mL, 1:3 v/v) was added and the temperature was maintained at 0° C. to induce NAS crystallization overnight (70% yield). 1H NMR (CDCl3) d (ppm): 2.95 (S, 4H, CH2CH2), 6.20 (m, 1H, CH═CH2), 6.4 (m, 1H, CH═CH2) and 6.75 (m, 1H, CH═CH2).

Preparation of random copolymers of DMA and NAS. General experimental conditions: DMA was distilled under reduced pressure prior to use. Monomers, t-BDB, initiator 2,2'-azobis(2-methylbutyronitrile) (AMBN) and solvent dioxane were introduced in a schlenk tube equipped with a magnetic stirrer. The mixture was degassed by three freeze-vacuum-thaw cycles and then heated under argon in a thermostated oil bath at 80° C. The percentage yields were calculated gravimetrically.

The structure of copolymers has been verified by application of appropriate chromatographic and spectrometric methods. Gel permeation chromatography (GPC) has been used to establish the molecular weight and molecular weight distribution of the copolymers. A Viscotek liquid chromatograph equipped with a Viscotek VE3210 UV/vis detector and a VE3580 reflective index detector and Viscotek GMHHR-M Viscogel™ GPC column was used. The flow rate was maintained at 0.5 mL min-1 using a Viscotek VE1121 GPC pump. 1-Methyl-2-pyrrolidinone was used as eluent. The molecular weights are provided as polystyrene equivalents. FIG. 15 is a flow chart of the RAFT polymerization procedure.

Preparation of copolymer containing 13 mol % of NAS units. NAS (0.81 g, 4.82 mmol), DMA (3.2 mL, 31 mmol), AMBN (70 mg, 0.36 mmol) and t-BDB (116 mg, 0.521 mmol) were added into 33 mL of 1,4-dioxane. The solution in a schlenk tube was degassed and heated at 80° C. for 18 hours. Then the solution was cooled and precipitated in 300 mL diethyl ether. The collected solid was redissolved in 1,4-dioxane and precipitated in diethyl ether. Yield of dried polymer was 75%. The molecular weight and polydispersity are shown in FIG. 8.

Preparation of copolymer containing 47 mol % of NAS units. NAS (2.33 g, 13.9 mmol), DMA (N,N-dimethylacrylamide 1.6 mL, 15.5 mmol), AMBN (70 mg, 0.36 mmol) and t-BDB (116 mg, 0.521 mmol) were added into 30 mL of 1,4-dioxane. The solution in a schlenk tube was degassed and heated at 80° C. for 18 hours. Some precipitation was observed in the tube. Then the solution was cooled and precipitated in 300 mL diethyl ether. The collected solid was redissolved in DMF and precipitated in diethyl ether. Yield of dried polymer was 80%. The molecular weight and polydispersity are shown in FIG. 8.

Preparation of copolymer containing 60 mol % of NAS units. It was prepared by a similar procedure as aforementioned (47 mol % of NAS units) one. More NAS monomer was added and solvent 1,4-dioxane was substituted by DMF. Yield of dried polymer was 80%. The molecular weight Mn and polydispersity Mw/Mn are shown in FIG. 8.

Example 2. Preparation of Ligand-Polymer Conjugate

Figure 9:
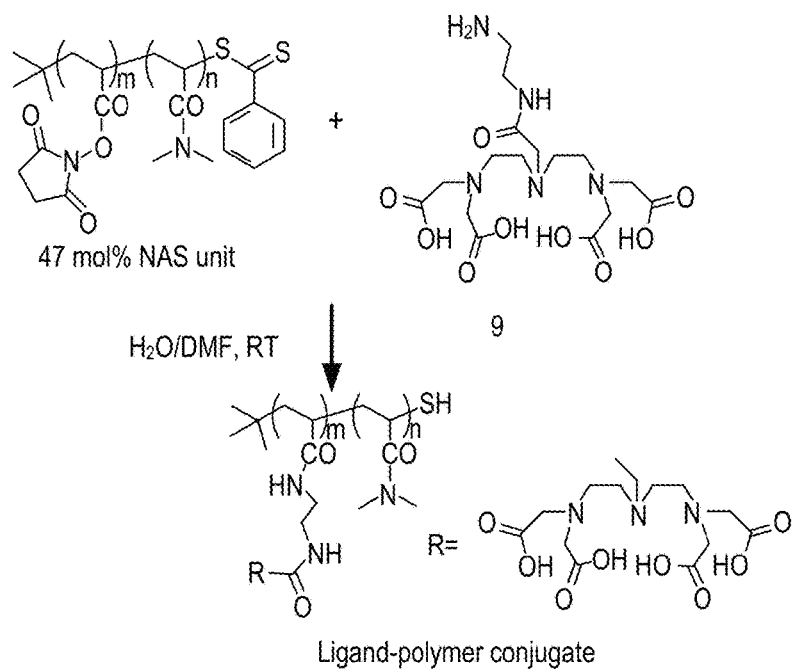
FIG. 9. Schematic views of preparation of ligand-polymer conjugate.
Figure 9:
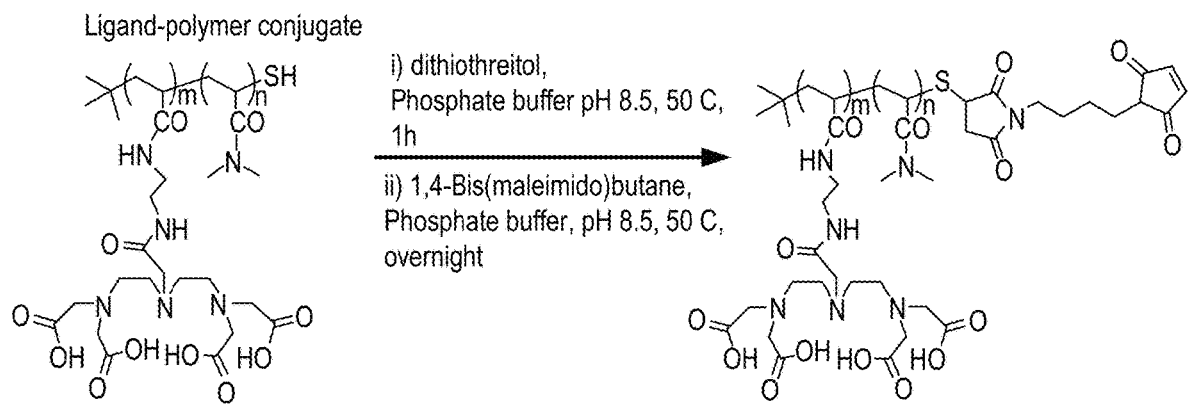

The following preparation of the polymer ligand conjugate is amenable for use with any amine functionalized ligand according to Scheme 10 and Scheme 11, FIG. 9.

To a stirred solution of the (N,N-dimethylacrylamide (DMA) and N-acryloxysuccinimide (NAS)) copolymer containing 47 mol % of NAS units (35 mg, 3.5461 mmol) and N,N-diisopropylethylamine (300 µl) in DMF/H2O (60:40, 1 mL) was added a solution of the amine pendant ligand 9, FIG. 9 (78 mg) in the same mixture (2 ml). The reaction mixture was stirred overnight under nitrogen at room temperature. The solvent was removed under vacuum and the solids were dissolved in $H_2O$. The solutions were dialyzed by repeated washings with deionized water (5×4 mL) in an Amicon centrifugal filter (5K MW C.O.) The solution remaining in the filter device was concentrated to give a yellowish solid. The solid was purified further by precipitation from methanol with diethylether to give a yellow powder (48 mg)

Ligand-polymer conjugate (5.5 mg) was dissolved in 1 mL of 50 mM phosphate buffer, (pH 8.5. 2 mL of 20 mM DTT) and the reaction mixture was stirred for 1 hour at 50° C. After the reaction, the mixture was made acidic (pH 4) with acetic acid and washed in an Amicon centrifugal filter (5K MW C.O.) with aqueous acetic acid (5 mM, 5×4 mL). The solution left in the filter device was then transferred to a small reaction flask containing 2 mL of 100 mM phosphate buffer, pH 8.5. A solution of 1,4-bis(maleimido)butane (50 equiv.; 32 mg) in DMF was added to the flask and the reaction mixture was stirred overnight at 50° C. The solvent was evaporated to give a residue, which was dissolved in $H_2O$, and the clear solution was again washed using an Amicon centrifugal filter (5K MW C.O.) with deionized water (5×5 mL). The supernatant was lyophilized to give the final conjugated polymer (4 mg).

Figure 10:
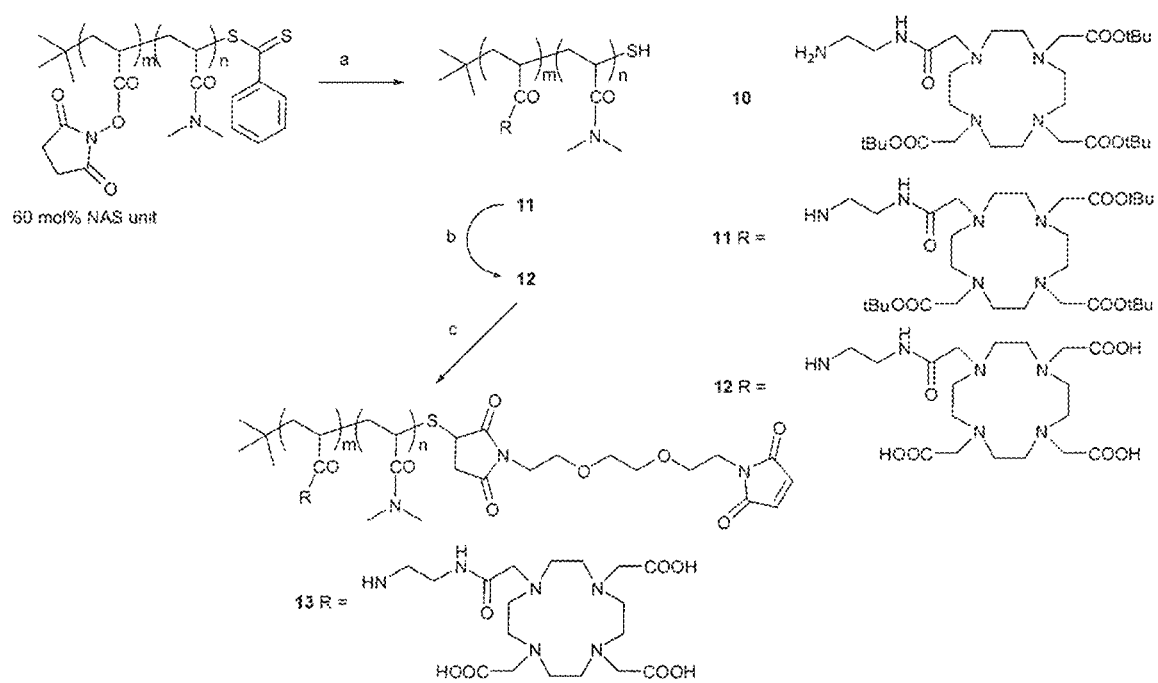
FIG. 10. Schematic views of preparation of the DOTA based ligand-polymer conjugate.

Example 3. Preparation of Ligand-Polymer Conjugate: DOTA Based Conjugate According to Scheme 12, FIG. 10

To a stirred solution of the DMA-NAS copolymer with 60 mol % of NAS units (100 mg) in DMF (3 mL) and triethylamine (1 mL) was added a solution of amine pendant ligand 10 (363 mg, 0.590 mmol) in DMF (2 mL). The reaction mixture was stirred overnight under nitrogen at room temperature. After the solvent was removed under vacuum, the residue 11 was dissolved in neat trifluoroacetic acid (3 mL) and stirred overnight at room temperature. The solution was evaporated, and the residue was taken up in water and dialyzed by repeated washings with deionized water (6×5 ml) in an Amicon centrifugal filter (5K MW C. O.). The solution remaining in the filter device (ca. 0.8 mL) was concentrated to give a yellow solid 12 (179 mg).

The entire sample of polymer-ligand conjugate 12 was dissolved in 50 mM phosphate buffer (pH 8.5, 2 mL) containing 20 mM DL-dithiothreitol, and the reaction mixture was stirred for 1 hour at 50° C. After this time, the mixture was acidified to pH 4 with acetic acid, and washed in an Amicon centrifugal filter (5 K MW C. O.) with aqueous acetic acid (5 mM, 5×5 mL). The solution left in the filter device (0.8 mL) was then transferred to a small reaction flask containing phosphate buffer (100 mM, pH 8.5, 5 mL). A solution of 2,2'-(Ethylenedioxy)bis(ethylmaleimide) (191 mg, 0.619 mmol) in DMF (2 mL) was added to the flask and the reaction mixture was stirred for 1 hour at room temperature. Water (3 mL) was added into the flask and the solid was removed by filtration. The resulting clear solution was again washed with deionized water (5×5 mL) using an Amicon centrifugal filter (5K MW C. O) and the supernatant was purified by Sephadex G-50 Column with HPLC system using water as an eluent. The fraction was collected and lyophilized to give the final conjugated polymer 13 (165.0 mg).

Example 4. Preparation of Ligand-Polymer Conjugate: DTPA Based Conjugate According to FIGS. 9, 11 and FIG. 16

To a stirred solution of the DMA-NAS copolymer with 60 mol % of NAS units (2.0 g) in DMF (30 mL) and triethylamine (4.3 mL) was added a solution of tert-butyl 2-aminoethylcarbamate, 14 (2.5 g, 15.6 mmol) in DMF (10 mL). The reaction mixture was stirred overnight under nitrogen at room temperature. Then the mixture was precipitated in 500 mL of diethyl ether. The collected solid 15 (400 mg) was dissolved in neat trifluoroacetic acid (3 mL) and stirred overnight at room temperature. The solution was evaporated, and the residue was taken up in water and dialyzed by repeated washings with deionized water (6×5 ml) in an Amicon centrifugal filter (5K MW C. O.). The solution remaining in the filter device (ca. 0.8 mL) was concentrated to give a yellow solid 16 (210 mg).

DTPA succinimidic ester was prepared according to a published procedure.[36] 16 g of DTPA (40.64 mmol) dissolved in 320 mL of Acetonitrile (23 g, 230 mmol of triethylamine added). Solution was stirred at 50° C. to dissolve the DTPA. 3.36 g of dicyclohexylcarbodiimide (DCC, 16.3 mmol) and 1.9 g of N-Hydroxysuccinimide (NHS, 16.3 mmol) were added simultaneously at room temperature. The reaction was carried out overnight. White precipitate was observed and filtered off by filtration paper, generating solution (A).

210 mg of solid 16 (ca. 0.8 mmol amino groups) was dissolved in 80 mL of distilled water and added into solution (A) at room temperature. 5 mL of triethylamine was added, and the solution was stirred at room temperature overnight. Solvents (triethylamine, acetonitrile) was then evaporated and 100 mL water added. The solution was dialyzed (1K cut-off membrane) for two days. Then the aqueous solution was concentrated, and acetic acid was added. It was dialyzed again with the same membrane for another three days. The solution is concentrated to give a solid 17 (190 mg).

Figure 16:
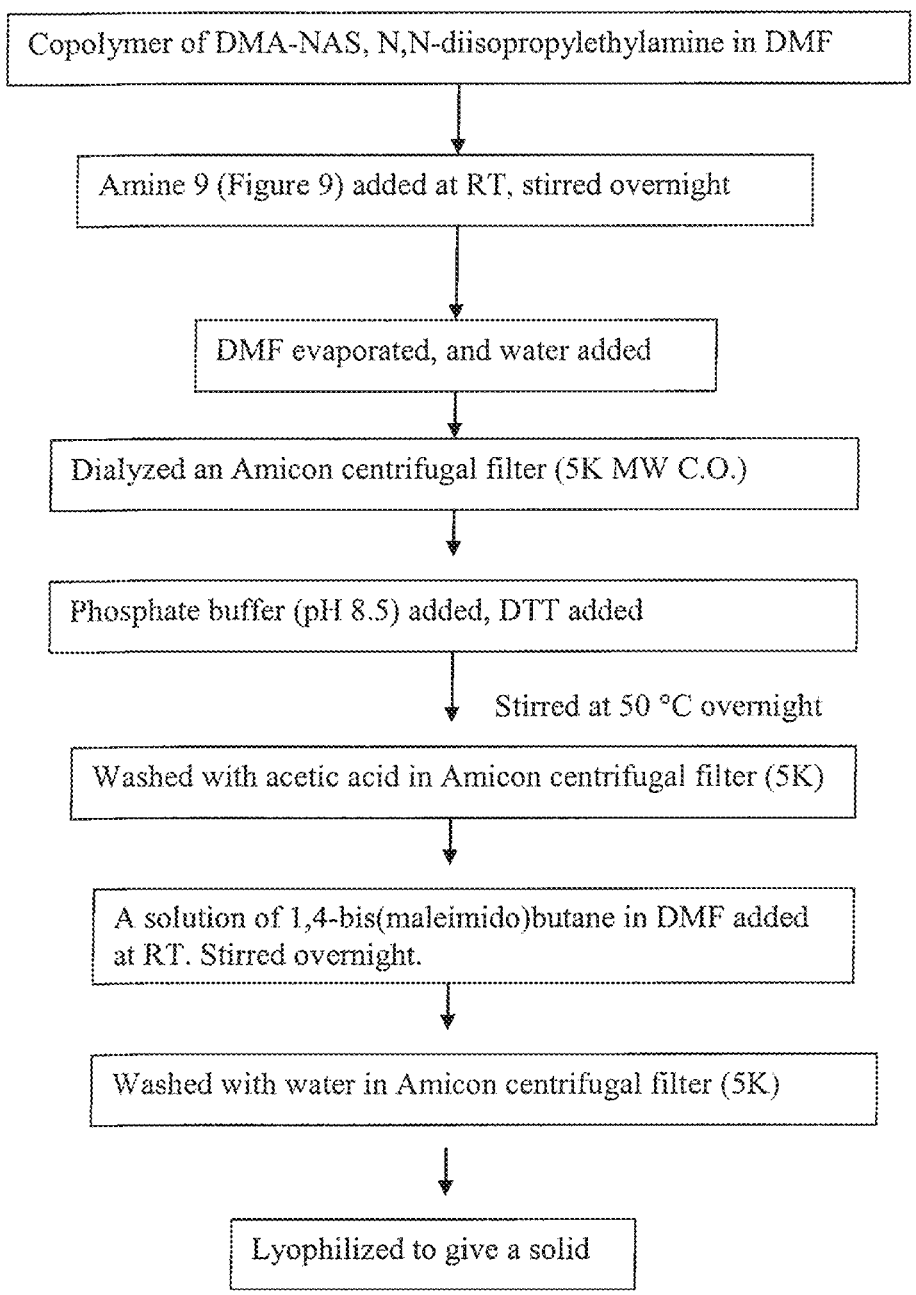
FIG. 16 is a flow Chart II of Polymer-DTPA-Linker attachment procedure.

Solid 17 (110 mg) was dissolved in 2.3 mL of phosphate buffer solution (pH 7.2). Then tri(2-carboxyethyl)phosphine (TCEP, 0.18 mL of 0.5 M solution) was added into buffer solution at room temperature. After the solution was stirred for 2 hours, it was added into 2,2'-(ethylenedioxy)-bis(ethylmaleimide) (0.36 mmol, 106 mg) in 2.3 mL of DMF at room temperature. 100 mL of distilled water was added after 2 hours and the solution was filtered through 5 k cut-off membrane with 5% DMSO/water (2 times) and then distilled water (3 times). The fraction was collected and lyophilized to give the final conjugated polymer 18 (90 mg). FIG. 16 is a flow chart showing the procedure for polymer-DTPA-linker attachment procedures.

Example 5. Preparation of Ligand-Polymer Conjugate: Poly(MAA) or Poly(AA)

Figure 11:
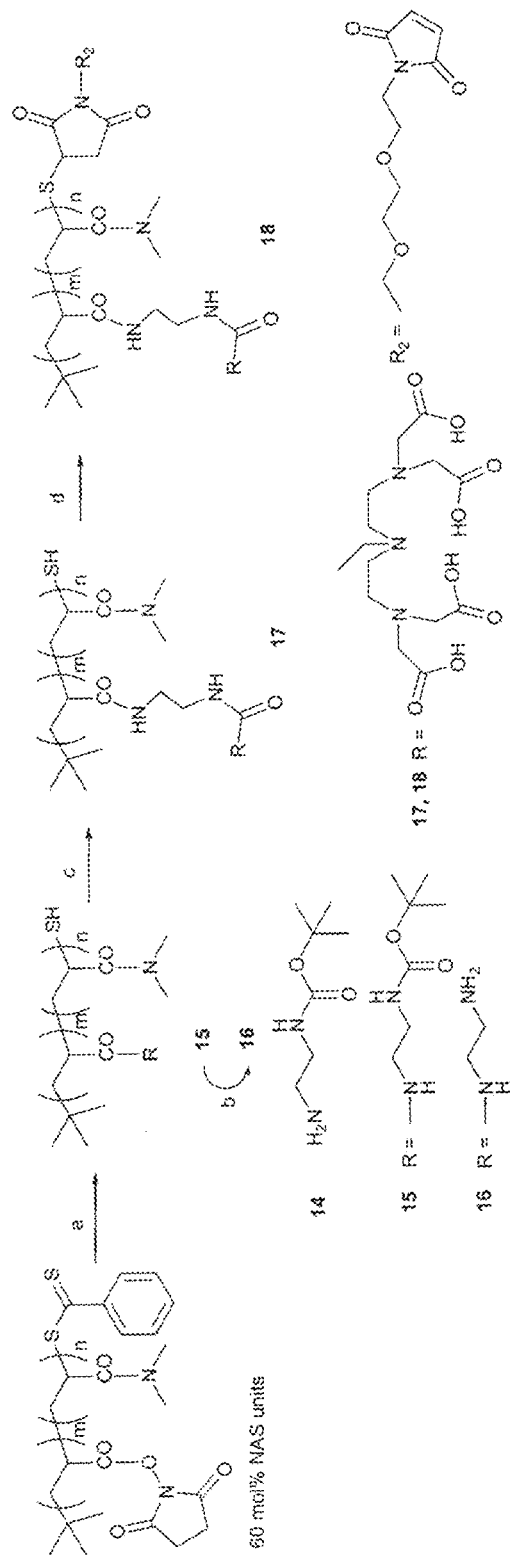
FIG. 11. Schematic views of synthesis of the element tag.
Figure 12:
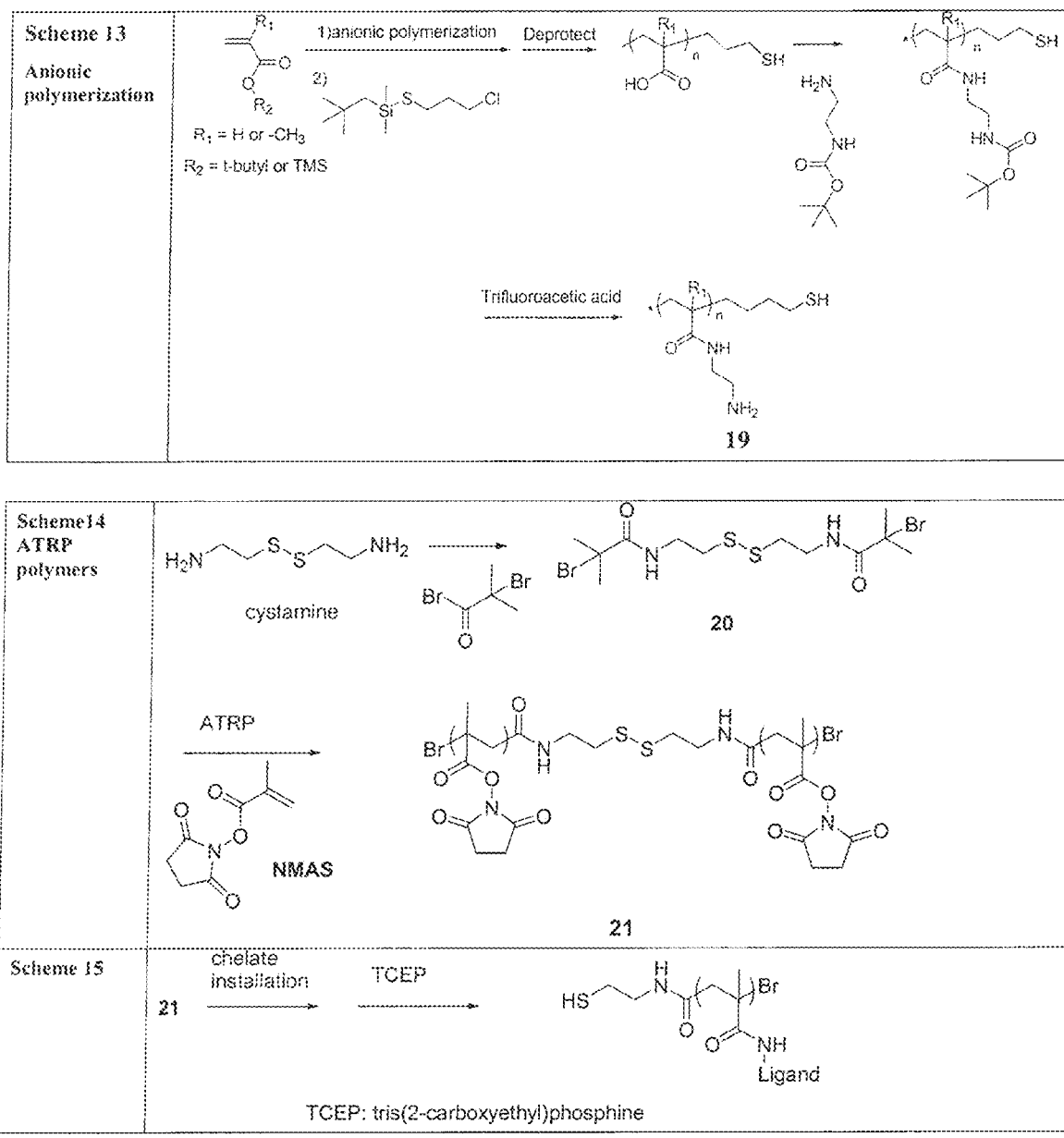
FIG. 12. Schematic views a process to generate a polymer with pendent amino groups for attachment of DTPA ligands and of employing a new initiator based on cystamine.

One aspect of the invention is related to specific functional advantages of polymer tags with a very narrow molar mass distribution. Polymethacrylic acid [Poly(MAA)] or polyacrylic acid [Poly(AA)] can be prepared by anionic polymerization of its t-butyl or trimethylsilyl (TMS) ester.[37] If the reaction is terminated with tert-butyldimethylsilyl 3-chloropropyl sulfide,[38] prior to ester hydrolysis (see below), the polymer will bear a protected —SH functional end group. They are reacted with tert-butyl 2-aminoethylcarbamate to form a polymer with protected amino groups, which is then hydrolyzed into polymer 19 (FIG. 12, Scheme 13). The free amino groups on main chain of polymer 19 offer sites for chelate attachment. The route for attaching chelate refers to the previous procedure using DTPA succinimidic ester (FIG. 11).

Poly(NMAS). Another approach has been reported by Müller[39] and used to attach drug conjugates to the polymer backbone. In this approach, NMAS was polymerized by ATRP, obtaining polymers with a mean molar mass ranging from 12 to 40 KDa with Mw/Mn of approximately 1.1. The initiator used was the hydroxyethyl ester of bromoisobutyric acid; thus the polymer chains all had a primary alcohol as an end group. Here, a new initiator based on cystamine 20 can be prepared (FIG. 12, Scheme 14). It is then used in the ATRP of NMAS to form a polymer 21 (FIG. 12, Scheme 14) with disulfide group. The polymer 21 can be reacted with tert-butyl 2-aminoethylcarbamate as shown in FIG. 12, Scheme 13 to generate a polymer with pendent amino groups for attachment of DTPA ligands. By using tri(2-carboxyethyl)phosphine (TCEP), the disulfide bond was reduced and a thiol end-group was generated for attachment of a linker to an antibody (FIG. 12, Scheme 15).

Example 6. Multiplex Labeling of Leukemia Cells

Figure 13:
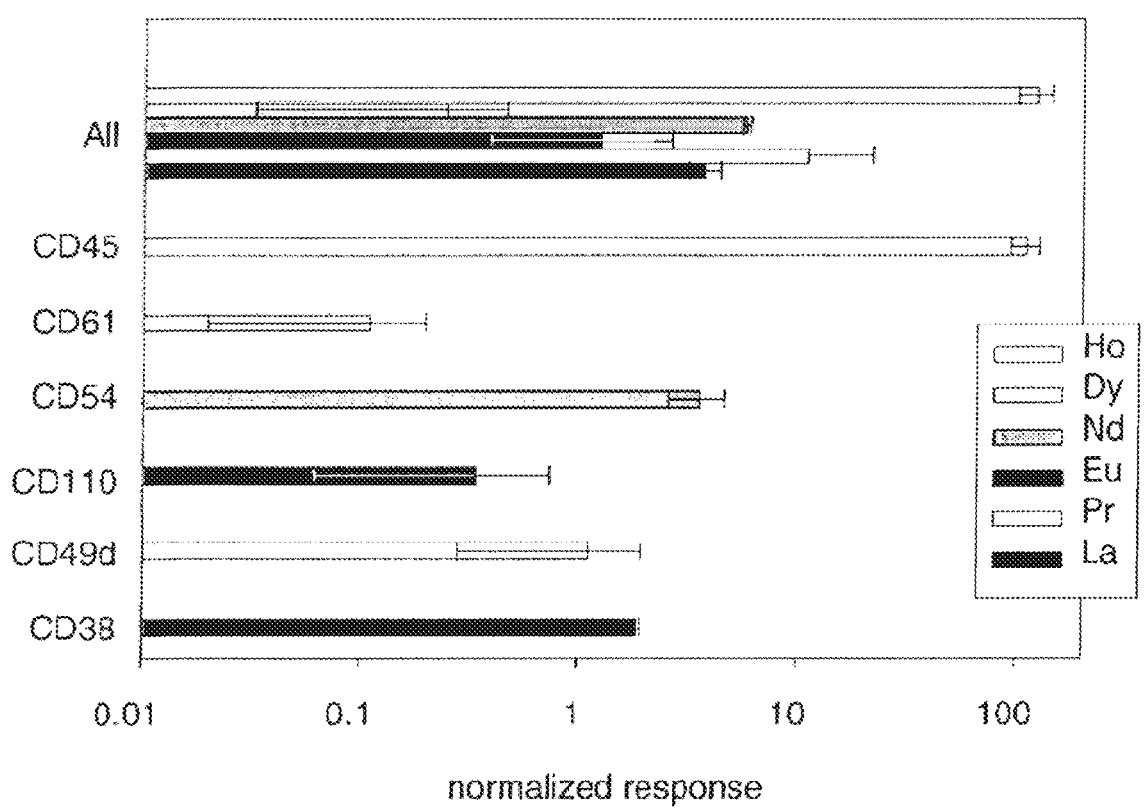
FIG. 13. Is a bar graph of the results of Experiment 6. Growing K562 cells (non-differentiated) were stained with primary antibodies labeled with Ligand-Polymer Conjugate (as described in Scheme 11)—carrying identifying lanthanides: anti-CD38 monoclonal antibody was labeled with La; anti-CD110—with Eu; anti-CD61—with Dy; anti-CD45—with Ho; anti-CD54—with Nd; CD49d—with Pr. Cells were reacted with labeled antibodies either with each separately, or with all antibodies simultaneously (ALL; 6-plexing). Note that the highly expressed ubiquitous nucleated blood cell marker CD45 (Ho) is on average 10 times greater than cell adhesion markers (CD54, Cd38, CD49d), and 100 times greater than megakaryocyte differentiation markers CD61 and CD110 (cells were not induced to differentiate along the megakaryocyte pathway).

K562 cells, a model cell line of human chronic myeloid leukemia, were cultured under standard tissue culture conditions in DMEM (Dulbecco's Modified Eagle's Medium) supplemented with 10% FBS (fetal bovine serum), 2 mM L-glutamine, and antibiotics. Growing cells were collected by low speed centrifugation (500×g), washed once with phosphate buffered saline (PBS), pH 7.4 and immunolabeled with primary antibodies attached to the metal-polymer conjugate (Ho, Dy, Nd, Eu, Pr, or La separately for each antibody) as described in Scheme 10 and Scheme 11 (FIG. 9). Six cell surface-specific antibodies were chosen for the experiment: CD38, CD110, CD61, CD45, CD54, CD49d. Aliquots of cells in triplicate tubes (0.3×106) were labeled with each antibody separately or with all antibodies combined in one reaction mixture (sample ALL). As negative control, mouse IgG1 isotype immunoglobulins were attached to metal-polymer conjugates carrying the same elements as the primary antibodies—Ho, Dy, Nd, Eu, Pr, or La. After 30 minutes incubation on ice, the cells were washed with PBS three times by centrifugation. The final cell pellet was dissolved in concentrated HCl (35%), mixed with an equal volume of 1 ppb Ir/HCl solution as internal standard and subjected to volume analysis ICP-MS. Results are presented in FIG. 13.

Antibodies were attached to the metal-polymer conjugate (synthesized according to Scheme 10 and Scheme 11, FIG. 9) according to the following protocol and reagents.

Reagents: Antibody at least 100-150 μg (~1 nmol) in 100 μl PBS/EDTA (~1 mg/ml). The antibodies were purchased commercially from BD Biosciences, San Jose, Calif.).

TCEP disulfide reducing gel (4% cross-linked agarose beads) from Pierce #77712; supplied as 50% slurry. Used at 1:1 50% slurry to antibody v/v.

Ligand-Polymer Conjugate (see Scheme 11, FIG. 9) dissolved in double distilled water (ddH$_2$O). Expected MW 11,000.

R-Buffer is 0.1M sodium phosphate pH 7.2, 2.5 mM EDTA

C-Buffer is TBS, 1 mM EDTA

L-Buffer is 20 mM ammonium acetate pH 6.0

Reduction of IgG Disulfide Bonds: Added 200 μL R-Buffer and 50 μg antibody solution to Diafiltration Membrane.

Centrifuged 10,000 g for 10 minutes. Discarded flow-through. Repeated once.

Added 100 μL R-Buffer and 0.8 μL 0.5M TCEP solution to Diafiltration Membrane and mixed gently (4 mM TCEP). Did not vortex.

Incubated 30 minutes at 37° C.

Added 200 μL C-Buffer. Centrifuged 10,000 g for 10 minutes. Discarded flow-through.

Labelling of Reduced IgG: Added 200 μL C-Buffer to membrane.

Prepared the element tag in C-Buffer at a concentration of 1 mM (1.1 mg element tag in 50 μL C-Buffer).

Added 10 μL of the prepared element tag to the tube containing 200 μL of the reduced IgG solution and mixed well. Did not vortex.

Allowed the reaction to proceed at least 1 hour at 37° C.

Added 200 μL L-Buffer to Membrane. Centrifuged 10,000 g for 10 minutes. Discarded flow-through. Repeated twice.

Added 100 μL L-Buffer to membrane to resuspend labelled antibody.

Added 5 μL of 0.1M lanthanide solution (prepared in Ultrapure Water as is known to those skilled in the art) to the antibody conjugated with the polymer tag. Mixed well. Did not vortex.

Incubated 30-60 minutes at 37° C.

Added 300 μL TBS. Centrifuged 10,000 g for 10 minutes. Discarded flow-through. Repeated three times.

Added 50 μL TBS. Gently pipetted several times to recover the conjugate and transfered to eppendorf tube.

Although ICP-MS was used in this analysis, it is to be understood that other forms of elemental analysis could have been used and are encompassed in the scope of the applicant's teachings.

Further, although leukemia cells were targeted as the analyte it is understood that any cell or particle can be analyzed in a similar manner.

Example 7. Analysis of Double Labeled Antibodies—Fluorescent Label and Element Tag In this example, the double labeled antibodies facilitate presorting and subsequent elemental analysis of rare cells in mixed samples by ICP-MS-based flow cytometry.

In one instance demonstration of data congruence collected by flow cytometry (FACS) and ICP-MS of cells stained with dually labelled antibodies (CD33-FITC-Pr) was conducted.

Figure 14:
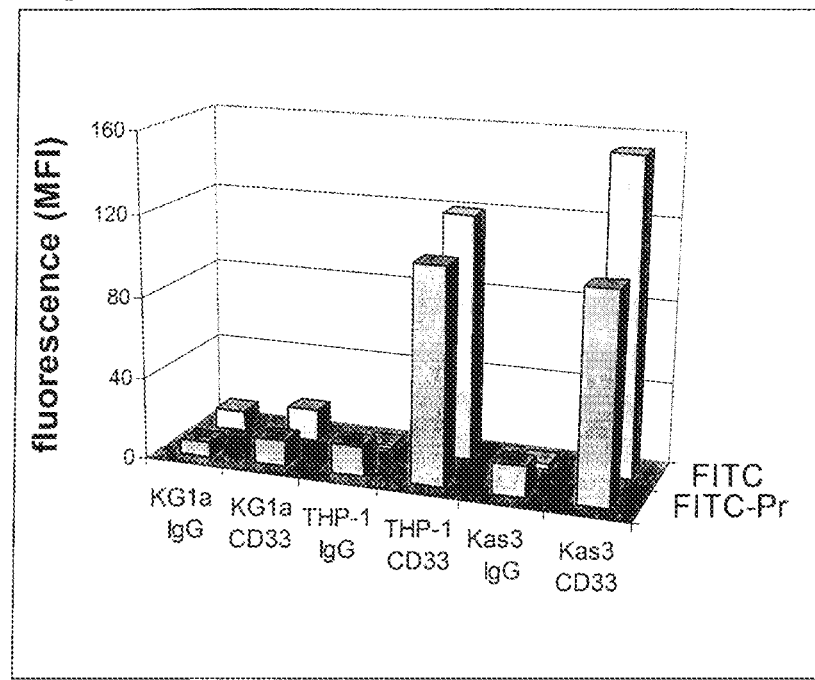
FIG. 14. a. Is a three-dimensional bar graph showing the direct comparison of fluorescence obtained from cells stained with CD33-FITC or dual labeled CD33-FITC-Pr using flow cytometry. b. Is a three-dimensional bar graph showing the direct comparison of normalized response obtained from cells stained with CD33-Pr or dual labeled CD33-FITC-Pr using ICP-MS.
Figure 14:
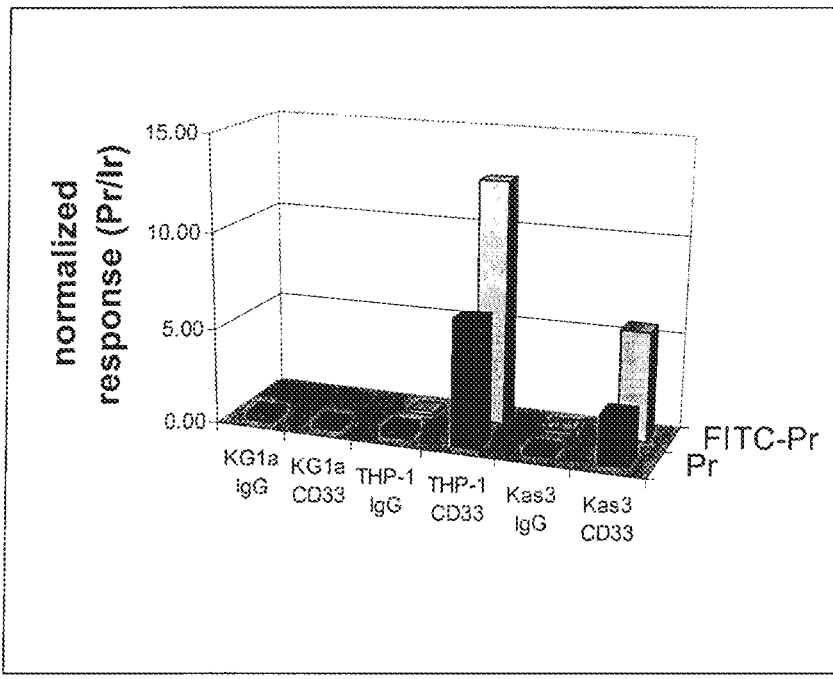

Monoclonal antibodies against cell surface antigen CD33 conjugated to fluoresceneisothiocyonate (FITC) (CD33-FITC; GenTex Inc.) were tagged with the polymer-DOTA-Pr construct. This dual labelled antibody will further be referred to as CD33-FITC-Pr. Several well characterized human leukemia cell lines (KG1a, THP-1, Kasumi-3; ATCC Inc) were used in cell staining studies. FACS analysis was performed on FACScalibur™ flow cytometer instrument (BD Biosciences Inc.) and ICP-MS data was obtained using ELAN DRCPlus (Perkin Elmer SCIEX). Live cells were washed by low speed centrifugation and incubated with CD33-FITC-Pr or CD33-FITC or CD33-Pr for antigen expression controls. Non-specific immunoglobulin binding was monitored with mouse IgG-FITC, IgG-Pr or dual labelled IgG-FITC-Pr. Data presented in FIG. 14a shows that fluorescence obtained from cells stained with dual labelled CD33-FITC-Pr are similar to CD33-FITC on all cell lines tested. Note that the KG1a cell line does not express CD33.

Likewise when CD33 expression was tested using element tagged antibodies CD33-Pr and dual labeled CD33-FITC-Pr (FIG. 14b), the normalized responses were similar.

Example 8. Particle Elemental Analysis Using a Mass Spectrometer Based Flow Cytometer The metal-polymer conjugate tags enable multiplexed assay in single cell format to distinguish a rare (for example a diseased) cell in a complex sample (for example, blood). The method can be used to identify leukemia cells in a patient's blood sample by employing metal-polymer tags conjugated to specific antibodies that recognize cell surface antigens present on the leukemia cells. For example, a positive multiplex staining of some cells in the peripheral blood mononuclear sample with antibodies against CD33, CD34, CD38, CD13, CD15, CD36 (tagged with different metals) and analyzed in a mass spectrometer based flow cytometer will indicate that the patient is developing acute monoblastic leukemia (AML-M5). In a similar manner, this method can be used to identify and quantify other cells, or particles.

Example 9. Kits

The invention encompasses kits useful for the preparation for the element tags and for carrying out the methods of the invention. The kits can include at least one of the following items:

a polymer comprising at least one metal-binding pendant group which contains at least one metal atom or is capable of binding at least one metal atom and further comprising a functional group that allows the polymer to be attached to one of a linker, a spacer, or a biomolecule, a metal solution, reagents for the attachment of the linker, spacer or biomolecule to the polymer, reagents for attachment of a functional group to the linker or the spacer, reagents for attachment of a metal to the polymer, affinity reagents including antibodies, buffers, instructions for preparing the element tag, instructions for attaching the element tag to an affinity reagent, instructions for attaching a metal to the element tag. and instructions for using the element tags for the analysis of analytes by elemental analysis. For example, the polymer can be homopolymers or copolymers of acrylamides, methacrylamides, acrylate esters, methacrylate esters, acrylic acid and methacrylic acid. The reagents can be chosen from at least one of the following: TCEP (tri(2-carboxyethyl) phosphine), Ligand-Polymer-Linker-Spacer Conjugate, phosphate buffer, TBS (tris-buffered saline), EDTA (Diaminoethanetetraacetic acid), ammonium acetate buffer, antibodies, metal salt solution, lanthanide salt solution, blocker buffers, washing buffers, FBS (fetal bovine serum), DMEM (Dulbecco's Modified Eagle's Medium), BSA (bovine serum albumin), dithiothreitol, bismaleimide, and DMF (dimethylformamide). The polymer can be provided which is attached to a linker or attached to both a linker and a spacer.

All references cited are incorporated by reference.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

REFERENCE LIST

1. Baranov, V. I.; Bandura, D. R.; Tanner, S. D. *European Winter Conference on Plasma Spectrochemistry*, Hafjell, Norway 2001, Book of Abstracts, p. 85.
2. Baranov, V. I.; Quinn, Z.; Bandura, D. R.; Tanner, S. D. *Anal. Chem.* 2002, 74, 1629-36.
3. Baranov, V. I.; Quinn, Z. A.; Bandura, D. R.; Tanner, S. D. *J. Anal. Atom. Spectrom.* 2002, 17, 1148-52.
4. Quinn, Z. A.; Baranov, V. I.; Tanner, S. D.; Wrana, J. L. *J. Anal. Atom. Spectrom.* 2002, 17, 892-96.

5. Baranov, V., Tanner, S., Bandura, D., and Quinn, Z. Kit for detecting/measuring transition element, comprising tag having transition element for tagging biologically active material and instruction for tagging material, combining tagged material with analyte, detecting/measuring elements. MDS, S. C. I. E. and MDS INC. [US2004072250-A1; WO2005003767-A2].

6. Baranov, V., Tanner, S., Bandura, D., and Quinn, Z. Detecting and measuring transition elements e.g. isotope or ions, in a sample, comprises tagging biologically active materials, and detecting and measuring reactant complexes by an atomic mass or optical spectrometer. MDS, S. C. I. E. and MDS INC. [WO200254075-A; EP1348127-A; US2002086441-A1; WO200254075-A1; EP1348127-A1; AU2002215784-A1; JP2004516490-W].

7. Baranov, V. I.; Quinn, Z.; Bandura, D. R.; Tanner, S. D. *Anal. Chem.* 2002, 74, 1629-36.

8. Bandura, D. R., Baranov, V., I, Tanner, S., and Tanner, S. D. Elemental flow cytometer, e.g. mass spectrometer or optical emission spectrometer based cytometer used in, e.g. health science, food sciences, environmental sciences, and genomics and proteomics, has spectrometer. Bandura, D. R., Baranov, V., I, Tanner, S., and MDS INC. [US2005218319-A1; WO2005093784-A1].

9. Hsu, K. C.; Zabriskie, J. B.; Rifkind, R. A. *Science* 1963, 142, 1471-&.

10. Powell, R. D.; Halsey, C. M. R.; Spector, D. L.; Kaurin, S. L.; McCann, J.; Hainfeld, J. F. *Journal of Histochemistry & Cytochemistry* 1997, 45, 947-56.

11. Riddle, S. M.; Vedvik, K. L.; Hanson, G. T.; Vogel, K. W. *Analytical Biochemistry* 2006, 356, 108-16.

12. Shunmugam, R.; Tew, G. N. *J. Am. Chem. Soc.* 2005, 127, 13567-72.

13. Chapman, A. P. *Advanced Drug Delivery Reviews* 2002, 54, 531-45.

14. Guddat, L. W.; Herron, J. N.; Edmundson, A. B. *Proc. Natl. Acad. Sci. U.S.A* 1993, 90, 4271-75.

15. Parker, D.; Dickins, R. S.; Puschmann, H.; Crossland, C.; Howard, J. A. *Chem. Rev.* 2002, 102, 1977-2010.

16. Liu, S.; Edwards, D. S. *Bioconjug. Chem.* 2001, 12, 7-34.

17. Caravan, P.; Ellison, J. J.; McMurry, T. J.; Lauffer, R. B. *Chem. Rev.* 1999, 99, 2293-352.

18. Baldwin, J. E.; North, M.; Flinn, A. *Tetrahedron* 1988, 44, 637-42.

19. Relogio, P.; Charreyre, M. T. C.; Farinha, J. S. P.; Martinho, J. M. G.; Pichot, C. *Polymer* 2004, 45, 8639-49.

20. Godwin, A.; Hartenstein, M.; Muller, A. H.; Brocchini, S. *Angew. Chem. Int. Ed Engl.* 2001, 40, 594-97.

21. Wang, X. S.; Dykstra, T. E.; Salvador, M. R.; Manners, I.; Scholes, G. D.; Winnik, M. A. *J. Am. Chem. Soc.* 2004, 126, 7784-85.

22. Shen, Y.; Zeng, F.; Zhu, S.; Pelton, R. *Macromolecules* 2001, 34, 144-50.

23. Woghiren, C.; Sharma, B.; Stein, S. *Bioconjug. Chem.* 1993, 4, 314-18.

24. Green, N. S.; Reisler, E.; Houk, K. N. *Protein Sci.* 2001, 10, 1293-304.

25. Godwin, A.; Hartenstein, M.; Muller, A. H.; Brocchini, S. *Angew. Chem. Int. Ed Engl.* 2001, 40, 594-97.

26. Hirao, A.; Hayashi, M. *Acta Polymerica* 1999, 50, 219-31.

27. Mizawa, T.; Takenaka, K.; Shiomi, T. *Journal of Polymer Science Part A: Polymer Chemistry* 2000, 38, 237-46.

28. Xie, H. Q.; Pan, S. B.; Guo, J. S. *European Polymer Journal* 2003, 39, 715-24.

29. Hild, G.; Lamps, J. P.; Rempp, P. *Polymer* 1993, 34, 2875-82.

30. Takenaka, K.; Hirao, A.; Nakahama, S. *Polymer International* 1995, 37, 291-95.

31. Cozzi, P. G.; Hilgraf, R.; Zimmermann, N. *European Journal of Organic Chemistry* 2004.

32. Roberts, M. J.; Bentley, M. D.; Harris, J. M. *Adv. Drug Deliv. Rev.* 2002, 54, 459-76.

33. Wu, P.; Feldman, A. K.; Nugent, A. K.; Hawker, C. J.; Scheel, A.; Voit, B.; Pyun, J.; Frechet, J. M.; Sharpless, K. B.; Fokin, V. V. *Angew. Chem. Int. Ed Engl.* 2004, 43, 3928-32.

34. Favier, A.; Charreyre, M. T.; Chaumont, P.; Pichot, C. *Macromolecules* 2002, 35, 8271-80.

35. D'Agosto, F.; Charreyre, M. T.; Pichot, C. *Macromolecular Bioscience* 2001, 1, 322-28.

36. Rebizak, R.; Schaefe, M.; Dellacherie, E. *Bioconjug. Chem.* 1997, 8, 605-10.

37. Mori, H.; Muller, A. H. *Prog. Polym. Sci* 2003, 28, 1403-39.

38. Tohyama, M.; Hirao, A.; Nakahama, S.; Takenaka, K. *Macromolecular Chemistry and Physics* 1996, 197, 3135-48.

39. Godwin, A.; Hartenstein, M.; Muller, A. H.; Brocchini, S. *Angew. Chem. Int. Ed Engl.* 2001, 40, 594-97.

What is claimed is:

1. A kit comprising:
    an isotopic composition comprising multiple lanthanide atoms of a single isotope of a lanthanide; and
    an element tag comprising a linear or branched polymer comprising a plurality of chelating groups, wherein each chelating group of the element tag includes at least one lanthanide atom of the isotopic composition or is capable of binding at least one lanthanide atom of the isotopic composition;
    wherein:
        the isotopic composition does not comprise a natural mixture of isotopes, and
        the kit does not comprise any radioactive lanthanide.

2. The kit of claim 1, wherein the element tag is functionalized to bind a biomolecule.

3. The kit of claim 1, wherein the element tag is covalently attached to a biomolecule.

4. The kit of claim 1, wherein the kit further comprises a biomolecule.

5. The kit of claim 4, wherein the biomolecule is an oligonucleotide.

6. The kit of claim 4, wherein the biomolecule is an antibody.

7. The kit of claim 1, wherein each chelating group includes at least one lanthanide atom of the isotopic composition.

8. The kit of claim 1, wherein the isotopic composition is a lanthanide solution provided separate from the element tag, and wherein each chelating group of the element tag is capable of binding at least one lanthanide atom of the isotopic composition.

9. The kit of claim 1, further comprising an additional isotopic composition, wherein the additional isotopic composition comprises multiple additional lanthanide atoms of an additional single isotope of a lanthanide that is different from the single isotope of the lanthanide of the isotopic composition.

10. The kit of claim 9, further comprising an additional element tag comprising an additional linear or branched polymer comprising a plurality of additional chelating groups.

11. The kit of claim 10, wherein each chelating group of the linear or branched polymer of the element tag includes at least one lanthanide atom of the isotopic composition, and wherein each additional chelating group of the additional linear or branched polymer of the additional element tag includes at least one additional lanthanide atom of the additional isotopic composition.

12. The kit of claim 11, wherein each element tag is covalently bound to a different antibody.

13. The kit of claim 1, wherein each chelating group is capable of binding at least one lanthanide atom of the isotopic composition, and each chelating group is selected from the group consisting of Diethylenetriaminepentaacetate (DTPA), 1,4,7,10-tetraazacyclododecane-1,4,7,10-tetraacetic acid (DOTA), a DTPA derivative, and a DOTA derivative.

14. The kit of claim 1, wherein each chelating group has a negative charge, when bound to a lanthanide atom.

15. The kit of claim 1, further comprising a reagent for covalent attachment of the element tag to an antibody.

* * * * *